(12) United States Patent
Bertness (10) Patent No.: US 7,728,597 B2
(45) Date of Patent: *Jun. 1, 2010

(54) ELECTRONIC BATTERY TESTER WITH DATABUS

(75) Inventor: Kevin I. Bertness, Batavia, IL (US)

(73) Assignee: Midtronics, Inc., Willowbrook, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/263,539

(22) Filed: Nov. 3, 2008

(65) Prior Publication Data

US 2009/0160451 A1 Jun. 25, 2009

Related U.S. Application Data

(63) Continuation of application No. 10/958,812, filed on Oct. 5, 2004, now Pat. No. 7,446,536, which is a continuation-in-part of application No. 10/460,749, filed on Jun. 12, 2003, now Pat. No. 6,967,484, which is a continuation-in-part of application No. 10/280,186, filed on Oct. 25, 2002, now Pat. No. 6,759,849, which is a continuation-in-part of application No. 09/816,768, filed on Mar. 23, 2001, now Pat. No. 6,586,941.

(60) Provisional application No. 60/192,222, filed on Mar. 27, 2000.

(51) Int. Cl.
*G01N 27/416* (2006.01)
(52) U.S. Cl. ...................................... 324/426
(58) Field of Classification Search ................ 324/426, 324/430, 433; 320/132, 149
See application file for complete search history.

(56) References Cited

U.S. PATENT DOCUMENTS

| 2,000,665 | A | 5/1935 | Neal | 439/440 |
| 2,417,940 | A | 3/1947 | Lehman | 200/61.25 |
| 2,514,745 | A | 7/1950 | Dalzell | 324/115 |
| 2,727,221 | A | 12/1955 | Springg | 340/447 |
| 3,178,686 | A | 4/1965 | Mills | 340/447 |
| 3,223,969 | A | 12/1965 | Alexander | 340/447 |
| 3,267,452 | A | 8/1966 | Wolf | 340/249 |

(Continued)

FOREIGN PATENT DOCUMENTS

DE 29 26 716 B1 1/1981

(Continued)

OTHER PUBLICATIONS

"Electrochemical Impedance Spectroscopy in Battery Development and Testing", *Batteries International*, Apr. 1997, pp. 59 and 62-63.

(Continued)

*Primary Examiner*—Edward Tso
(74) *Attorney, Agent, or Firm*—Westman, Champlin & Kelly, P.A.

(57) ABSTRACT

A cable for connecting to an electronic battery tester, includes a first end configured to couple to a databus of a vehicle and a second end configured to couple to the electronic battery tester. An electrical connection extends between the first end and the second end and is configured to couple the electronic battery tester to the databus of the vehicle.

14 Claims, 7 Drawing Sheets

U.S. PATENT DOCUMENTS

| | | | | |
|---|---|---|---|---|
| 3,356,936 A | 12/1967 | Smith | | 324/429 |
| 3,562,634 A | 2/1971 | Latner | | 324/427 |
| 3,593,099 A | 7/1971 | Scholl | | 320/127 |
| 3,607,673 A | 9/1971 | Seyl | | 324/425 |
| 3,652,341 A | 3/1972 | Halsall et al. | | 29/623.2 |
| 3,676,770 A | 7/1972 | Sharaf et al. | | 324/430 |
| 3,729,989 A | 5/1973 | Little | | 73/862.192 |
| 3,750,011 A | 7/1973 | Kreps | | 324/430 |
| 3,753,094 A | 8/1973 | Furuishi et al. | | 324/430 |
| 3,776,177 A | 12/1973 | Bryant et al. | | 116/311 |
| 3,796,124 A | 3/1974 | Crosa | | 411/521 |
| 3,808,522 A | 4/1974 | Sharaf | | 324/430 |
| 3,811,089 A | 5/1974 | Strezelewicz | | 324/170 |
| 3,816,805 A | 6/1974 | Terry | | 320/123 |
| 3,850,490 A | 11/1974 | Zehr | | 439/822 |
| 3,873,911 A | 3/1975 | Champlin | | 324/430 |
| 3,876,931 A | 4/1975 | Godshalk | | 324/429 |
| 3,886,426 A | 5/1975 | Daggett | | 320/117 |
| 3,886,443 A | 5/1975 | Miyakawa et al. | | 324/426 |
| 3,889,248 A | 6/1975 | Ritter | | 340/636.11 |
| 3,906,329 A | 9/1975 | Bader | | 320/134 |
| 3,909,708 A | 9/1975 | Champlin | | 324/431 |
| 3,936,744 A | 2/1976 | Perlmutter | | 324/772 |
| 3,946,299 A | 3/1976 | Christianson et al. | | 320/430 |
| 3,947,757 A | 3/1976 | Grube et al. | | 324/416 |
| 3,969,667 A | 7/1976 | McWilliams | | 324/427 |
| 3,979,664 A | 9/1976 | Harris | | 324/397 |
| 3,984,762 A | 10/1976 | Dowgiallo, Jr. | | 324/430 |
| 3,984,768 A | 10/1976 | Staples | | 324/712 |
| 3,989,544 A | 11/1976 | Santo | | 429/65 |
| 4,008,619 A | 2/1977 | Alcaide et al. | | 73/724 |
| 4,023,882 A | 5/1977 | Pettersson | | 439/426 |
| 4,024,953 A | 5/1977 | Nailor, III | | 206/344 |
| 4,047,091 A | 9/1977 | Hutchines et al. | | 363/59 |
| 4,053,824 A | 10/1977 | Dupuis et al. | | 324/434 |
| 4,056,764 A | 11/1977 | Endo et al. | | 320/101 |
| 4,057,313 A | 11/1977 | Polizzano | | 439/219 |
| 4,070,624 A | 1/1978 | Taylor | | 324/772 |
| 4,086,531 A | 4/1978 | Bernier | | 324/772 |
| 4,106,025 A | 8/1978 | Katz | | 343/715 |
| 4,112,351 A | 9/1978 | Back et al. | | 324/380 |
| 4,114,083 A | 9/1978 | Benham et al. | | 340/636.13 |
| 4,126,874 A | 11/1978 | Suzuki et al. | | 396/301 |
| 4,160,916 A | 7/1979 | Papasideris | | 307/10.6 |
| 4,178,546 A | 12/1979 | Hulls et al. | | 324/772 |
| 4,193,025 A | 3/1980 | Frailing et al. | | 324/427 |
| 4,207,611 A | 6/1980 | Gordon | | 701/33 |
| 4,217,645 A | 8/1980 | Barry et al. | | 702/63 |
| 4,280,457 A | 7/1981 | Bloxham | | 123/198 R |
| 4,297,639 A | 10/1981 | Branham | | 324/429 |
| 4,307,342 A | 12/1981 | Peterson | | 324/767 |
| 4,315,204 A | 2/1982 | Sievers et al. | | 322/28 |
| 4,316,185 A | 2/1982 | Watrous et al. | | 340/636.11 |
| 4,322,685 A | 3/1982 | Frailing et al. | | 324/429 |
| 4,351,405 A | 9/1982 | Fields et al. | | 180/65.2 |
| 4,352,067 A | 9/1982 | Ottone | | 324/434 |
| 4,360,780 A | 11/1982 | Skutch, Jr. | | 324/437 |
| 4,361,809 A | 11/1982 | Bil et al. | | 324/426 |
| 4,363,407 A | 12/1982 | Buckler et al. | | 209/3.3 |
| 4,369,407 A | 1/1983 | Korbell | | 324/416 |
| 4,379,989 A | 4/1983 | Kurz et al. | | 320/165 |
| 4,379,990 A | 4/1983 | Sievers et al. | | 322/99 |
| 4,385,269 A | 5/1983 | Aspinwall et al. | | 320/129 |
| 4,390,828 A | 6/1983 | Converse et al. | | 320/153 |
| 4,392,101 A | 7/1983 | Saar et al. | | 320/156 |
| 4,396,880 A | 8/1983 | Windebank | | 320/156 |
| 4,408,157 A | 10/1983 | Beaubien | | 324/712 |
| 4,412,169 A | 10/1983 | Dell'Orto | | 320/123 |
| 4,423,378 A | 12/1983 | Marino et al. | | 324/427 |
| 4,423,379 A | 12/1983 | Jacobs et al. | | 324/430 |
| 4,424,491 A | 1/1984 | Bobbett et al. | | 324/433 |
| 4,441,359 A | 4/1984 | Ezoe | | 73/116.06 |
| 4,459,548 A | 7/1984 | Lentz et al. | | 324/472 |
| 4,514,694 A | 4/1985 | Finger | | 324/429 |
| 4,520,353 A | 5/1985 | McAuliffe | | 340/636.16 |
| 4,521,498 A | 6/1985 | Juergens | | 429/59 |
| 4,564,798 A | 1/1986 | Young | | 320/103 |
| 4,620,767 A | 11/1986 | Woolf | | 439/217 |
| 4,633,418 A | 12/1986 | Bishop | | 702/63 |
| 4,637,359 A | 1/1987 | Cook | | 123/179 |
| 4,659,977 A | 4/1987 | Kissel et al. | | 320/150 |
| 4,663,580 A | 5/1987 | Wortman | | 320/153 |
| 4,665,370 A | 5/1987 | Holland | | 324/429 |
| 4,667,143 A | 5/1987 | Cooper et al. | | 320/153 |
| 4,667,279 A | 5/1987 | Maier | | 363/46 |
| 4,678,998 A | 7/1987 | Muramatsu | | 324/427 |
| 4,679,000 A | 7/1987 | Clark | | 324/428 |
| 4,680,528 A | 7/1987 | Mikami et al. | | 320/165 |
| 4,686,442 A | 8/1987 | Radomski | | 320/123 |
| 4,697,134 A | 9/1987 | Burkum et al. | | 320/134 |
| 4,707,795 A | 11/1987 | Alber et al. | | 702/63 |
| 4,709,202 A | 11/1987 | Koenck et al. | | 320/112 |
| 4,710,861 A | 12/1987 | Kanner | | 363/46 |
| 4,719,428 A | 1/1988 | Liebermann | | 324/436 |
| 4,723,656 A | 2/1988 | Kiernan et al. | | 206/705 |
| 4,743,855 A | 5/1988 | Randin et al. | | 324/430 |
| 4,745,349 A | 5/1988 | Palanisamy et al. | | 320/125 |
| 4,773,011 A | 9/1988 | VanHoose | | 701/30 |
| 4,781,629 A | 11/1988 | Mize | | 439/822 |
| 4,816,768 A | 3/1989 | Champlin | | 324/428 |
| 4,820,966 A | 4/1989 | Fridman | | 320/116 |
| 4,825,170 A | 4/1989 | Champlin | | 324/436 |
| 4,847,547 A | 7/1989 | Eng, Jr. et al. | | 320/153 |
| 4,849,700 A | 7/1989 | Morioka et al. | | 324/427 |
| 4,874,679 A | 10/1989 | Miyagawa | | 429/91 |
| 4,876,495 A | 10/1989 | Palanisamy et al. | | 320/106 |
| 4,881,038 A | 11/1989 | Champlin | | 324/426 |
| 4,888,716 A | 12/1989 | Ueno | | 702/63 |
| 4,901,007 A | 2/1990 | Sworm | | 324/110 |
| 4,907,176 A | 3/1990 | Bahnick et al. | | 364/551.01 |
| 4,912,416 A | 3/1990 | Champlin | | 324/430 |
| 4,913,116 A | 4/1990 | Katogi et al. | | 123/406.32 |
| 4,926,330 A | 5/1990 | Abe et al. | | 701/33 |
| 4,929,931 A | 5/1990 | McCuen | | 340/636.15 |
| 4,931,738 A | 6/1990 | MacIntyre et al. | | 324/435 |
| 4,932,905 A | 6/1990 | Richards | | 439/822 |
| 4,933,845 A | 6/1990 | Hayes | | 710/104 |
| 4,934,957 A | 6/1990 | Bellusci | | 439/504 |
| 4,937,528 A | 6/1990 | Palanisamy | | 324/430 |
| 4,947,124 A | 8/1990 | Hauser | | 324/430 |
| 4,949,046 A | 8/1990 | Seyfang | | 324/427 |
| 4,956,597 A | 9/1990 | Heavey et al. | | 320/129 |
| 4,968,941 A | 11/1990 | Rogers | | 324/428 |
| 4,968,942 A | 11/1990 | Palanisamy | | 324/430 |
| 4,969,834 A | 11/1990 | Johnson | | 439/141 |
| 4,983,086 A | 1/1991 | Hatrock | | 411/259 |
| 5,004,979 A | 4/1991 | Marino et al. | | 324/160 |
| 5,032,825 A | 7/1991 | Kuznicki | | 340/636.15 |
| 5,034,893 A | 7/1991 | Fisher | | 701/99 |
| 5,037,778 A | 8/1991 | Stark et al. | | 228/121 |
| 5,047,722 A | 9/1991 | Wurst et al. | | 324/430 |
| 5,081,565 A | 1/1992 | Nabha et al. | | 362/465 |
| 5,087,881 A | 2/1992 | Peacock | | 324/378 |
| 5,095,223 A | 3/1992 | Thomas | | 307/110 |
| 5,108,320 A | 4/1992 | Kimber | | 439/883 |
| 5,109,213 A | 4/1992 | Williams | | 340/447 |
| 5,126,675 A | 6/1992 | Yang | | 324/435 |
| 5,130,658 A | 7/1992 | Bohmer | | 324/435 |
| 5,140,269 A | 8/1992 | Champlin | | 324/433 |
| 5,144,218 A | 9/1992 | Bosscha | | 320/139 |
| 5,144,248 A | 9/1992 | Alexandres et al. | | 324/428 |
| 5,159,272 A | 10/1992 | Rao et al. | | 324/429 |
| 5,160,881 A | 11/1992 | Schramm et al. | | 322/7 |
| 5,168,208 A | 12/1992 | Schultz et al. | | 322/25 |

| | | | | | | | |
|---|---|---|---|---|---|---|---|
| 5,170,124 A | 12/1992 | Blair et al. | 324/434 | 5,578,915 A | 11/1996 | Crouch, Jr. et al. | 324/428 |
| 5,179,335 A | 1/1993 | Nor | 320/159 | 5,583,416 A | 12/1996 | Klang | 320/160 |
| 5,194,799 A | 3/1993 | Tomantschger | 320/103 | 5,585,416 A | 12/1996 | Audett et al. | 522/35 |
| 5,204,611 A | 4/1993 | Nor et al. | 320/145 | 5,585,728 A | 12/1996 | Champlin | 324/427 |
| 5,214,370 A | 5/1993 | Harm et al. | 320/152 | 5,589,757 A | 12/1996 | Klang | 320/160 |
| 5,214,385 A | 5/1993 | Gabriel et al. | 324/434 | 5,592,093 A | 1/1997 | Klingbiel | 324/426 |
| 5,241,275 A | 8/1993 | Fang | 324/430 | 5,592,094 A | 1/1997 | Ichikawa | 324/427 |
| 5,254,952 A | 10/1993 | Salley et al. | 324/429 | 5,596,260 A | 1/1997 | Moravec et al. | 320/135 |
| 5,266,880 A | 11/1993 | Newland | 320/125 | 5,598,098 A | 1/1997 | Champlin | 324/430 |
| 5,281,919 A | 1/1994 | Palanisamy | 324/427 | 5,602,462 A | 2/1997 | Stich et al. | 323/258 |
| 5,281,920 A | 1/1994 | Wurst | 324/430 | 5,606,242 A | 2/1997 | Hull et al. | 320/106 |
| 5,295,078 A | 3/1994 | Stich et al. | 700/297 | 5,614,788 A | 3/1997 | Mullins et al. | 315/82 |
| 5,298,797 A | 3/1994 | Redl | 327/387 | 5,621,298 A | 4/1997 | Harvey | 320/134 |
| 5,300,874 A | 4/1994 | Shimamoto et al. | 320/106 | 5,633,985 A | 5/1997 | Severson et al. | 704/267 |
| 5,302,902 A | 4/1994 | Groehl | 324/434 | 5,637,978 A | 6/1997 | Kellett et al. | 320/104 |
| 5,313,152 A | 5/1994 | Wozniak et al. | 320/118 | 5,642,031 A | 6/1997 | Brotto | 320/156 |
| 5,315,287 A | 5/1994 | Sol | 340/455 | 5,650,937 A | 7/1997 | Bounaga | 702/65 |
| 5,321,626 A | 6/1994 | Palladino | 702/63 | 5,652,501 A | 7/1997 | McClure et al. | 340/636.15 |
| 5,321,627 A | 6/1994 | Reher | 702/63 | 5,653,659 A | 8/1997 | Kunibe et al. | 477/111 |
| 5,323,337 A | 6/1994 | Wilson et al. | 702/73 | 5,654,623 A | 8/1997 | Shiga et al. | 320/106 |
| 5,325,041 A | 6/1994 | Briggs | 320/149 | 5,656,920 A | 8/1997 | Cherng et al. | 324/431 |
| 5,331,268 A | 7/1994 | Patino et al. | 320/158 | 5,661,368 A | 8/1997 | Deol et al. | 315/82 |
| 5,332,927 A | 7/1994 | Paul et al. | 307/66 | 5,675,234 A | 10/1997 | Greene | 340/636.11 |
| 5,336,993 A | 8/1994 | Thomas et al. | 324/158.1 | 5,677,077 A | 10/1997 | Faulk | 429/90 |
| 5,338,515 A | 8/1994 | Dalla Betta et al. | 422/95 | 5,684,678 A | 11/1997 | Barrett | 363/17 |
| 5,339,018 A | 8/1994 | Brokaw | 320/147 | 5,699,050 A | 12/1997 | Kanazawa | 340/636.13 |
| 5,343,380 A | 8/1994 | Champlin | 363/46 | 5,701,089 A | 12/1997 | Perkins | 324/772 |
| 5,347,163 A | 9/1994 | Yoshimura | 307/66 | 5,705,929 A | 1/1998 | Caravello et al. | 324/430 |
| 5,352,968 A | 10/1994 | Reni et al. | 320/136 | 5,707,015 A | 1/1998 | Guthrie | 241/120 |
| 5,357,519 A | 10/1994 | Martin et al. | 371/15.1 | 5,710,503 A | 1/1998 | Sideris et al. | 320/116 |
| 5,365,160 A | 11/1994 | Leppo et al. | 320/160 | 5,711,648 A | 1/1998 | Hammerslag | 414/800 |
| 5,365,453 A | 11/1994 | Startup et al. | 702/36 | 5,717,336 A | 2/1998 | Basell et al. | 324/430 |
| 5,369,364 A | 11/1994 | Renirie et al. | 324/430 | 5,717,937 A | 2/1998 | Fritz | 713/300 |
| 5,381,096 A | 1/1995 | Hirzel | 324/427 | 5,739,667 A | 4/1998 | Matsuda et al. | 320/128 |
| 5,387,871 A | 2/1995 | Tsai | 324/429 | 5,744,962 A | 4/1998 | Alber et al. | 324/426 |
| 5,402,007 A | 3/1995 | Center et al. | 290/40 B | 5,745,044 A | 4/1998 | Hyatt, Jr. et al. | 340/5.23 |
| 5,410,754 A | 4/1995 | Klotzbach et al. | 370/466 | 5,747,189 A | 5/1998 | Perkins | 429/91 |
| 5,412,308 A | 5/1995 | Brown | 323/267 | 5,747,909 A | 5/1998 | Syverson et al. | 310/156.56 |
| 5,412,323 A | 5/1995 | Kato et al. | 324/429 | 5,747,967 A | 5/1998 | Muljadi et al. | 320/148 |
| 5,425,041 A | 6/1995 | Seko et al. | 372/45.01 | 5,754,417 A | 5/1998 | Nicollini | 363/60 |
| 5,426,371 A | 6/1995 | Salley et al. | 324/429 | 5,757,192 A | 5/1998 | McShane et al. | 324/427 |
| 5,426,416 A | 6/1995 | Jefferies et al. | 340/664 | 5,760,587 A | 6/1998 | Harvey | 324/434 |
| 5,430,645 A | 7/1995 | Keller | 364/424.01 | 5,772,468 A | 6/1998 | Kowalski et al. | 439/506 |
| 5,432,025 A | 7/1995 | Cox | 429/65 | 5,773,978 A | 6/1998 | Becker | 324/430 |
| 5,432,426 A | 7/1995 | Yoshida | 320/160 | 5,778,326 A | 7/1998 | Moroto et al. | 701/22 |
| 5,434,495 A | 7/1995 | Toko | 320/135 | 5,780,974 A | 7/1998 | Pabla et al. | 315/82 |
| 5,435,185 A | 7/1995 | Eagan | 73/587 | 5,780,980 A | 7/1998 | Naito | 318/139 |
| 5,442,274 A | 8/1995 | Tamai | 320/146 | 5,789,899 A | 8/1998 | van Phuoc et al. | 320/112 |
| 5,445,026 A | 8/1995 | Eagan | 73/591 | 5,793,359 A | 8/1998 | Ushikubo | 345/169 |
| 5,449,996 A | 9/1995 | Matsumoto et al. | 320/148 | 5,796,239 A | 8/1998 | van Phuoc et al. | 320/107 |
| 5,449,997 A | 9/1995 | Gilmore et al. | 320/148 | 5,808,469 A | 9/1998 | Kopera | 324/434 |
| 5,451,881 A | 9/1995 | Finger | 324/433 | 5,811,979 A | 9/1998 | Rhein | 324/718 |
| 5,453,027 A | 9/1995 | Buell et al. | 439/433 | 5,818,234 A | 10/1998 | McKinnon | 324/433 |
| 5,457,377 A | 10/1995 | Jonsson | 324/430 | 5,820,407 A | 10/1998 | Morse et al. | 439/504 |
| 5,459,660 A | 10/1995 | Berra | 701/33 | 5,821,756 A | 10/1998 | McShane et al. | 324/430 |
| 5,469,043 A | 11/1995 | Cherng et al. | 320/161 | 5,821,757 A | 10/1998 | Alvarez et al. | 324/434 |
| 5,485,090 A | 1/1996 | Stephens | 324/433 | 5,825,174 A | 10/1998 | Parker | 324/106 |
| 5,488,300 A | 1/1996 | Jamieson | 324/432 | 5,831,435 A | 11/1998 | Troy | 324/426 |
| 5,504,674 A | 4/1996 | Chen et al. | 705/4 | 5,832,396 A | 11/1998 | Moroto et al. | 701/22 |
| 5,508,599 A | 4/1996 | Koenck | 320/138 | 5,850,113 A | 12/1998 | Weimer et al. | 307/125 |
| 5,519,383 A | 5/1996 | De La Rosa | 340/636.15 | 5,862,515 A | 1/1999 | Kobayashi et al. | 702/63 |
| 5,528,148 A | 6/1996 | Rogers | 320/137 | 5,865,638 A | 2/1999 | Trafton | 439/288 |
| 5,537,967 A | 7/1996 | Tashiro et al. | 123/192.1 | 5,871,858 A | 2/1999 | Thomsen et al. | 429/7 |
| 5,541,489 A | 7/1996 | Dunstan | 320/134 | 5,872,443 A | 2/1999 | Williamson | 320/160 |
| 5,546,317 A | 8/1996 | Andrieu | 702/63 | 5,872,453 A | 2/1999 | Shimoyama et al. | 321/431 |
| 5,548,273 A | 8/1996 | Nicol et al. | 340/439 | 5,883,306 A | 3/1999 | Hwang | 73/146.8 |
| 5,550,485 A | 8/1996 | Falk | 324/772 | 5,895,440 A | 4/1999 | Proctor et al. | 702/63 |
| 5,561,380 A | 10/1996 | Sway-Tin et al. | 324/509 | 5,903,154 A | 5/1999 | Zhang et al. | 324/437 |
| 5,562,501 A | 10/1996 | Kinoshita et al. | 439/852 | 5,903,716 A | 5/1999 | Kimber et al. | 395/114 |
| 5,563,496 A | 10/1996 | McClure | 320/128 | 5,912,534 A | 6/1999 | Benedict | 315/82 |
| 5,572,136 A | 11/1996 | Champlin | 324/426 | 5,914,605 A | 6/1999 | Bertness | 324/430 |
| 5,573,611 A | 11/1996 | Koch et al. | 152/152.1 | 5,927,938 A | 7/1999 | Hammerslag | 414/809 |
| 5,574,355 A | 11/1996 | McShane et al. | 320/161 | 5,929,609 A | 7/1999 | Joy et al. | 322/25 |

| | | | | | | | |
|---|---|---|---|---|---|---|---|
| 5,939,855 A | 8/1999 | Proctor et al. | 320/104 | 6,271,643 B1 | 8/2001 | Becker et al. | 320/112 |
| 5,939,861 A | 8/1999 | Joko et al. | 320/122 | 6,271,748 B1 | 8/2001 | Derbyshire et al. | 340/442 |
| 5,945,829 A | 8/1999 | Bertness | 324/430 | 6,275,008 B1 | 8/2001 | Arai et al. | 320/132 |
| 5,946,605 A | 8/1999 | Takahisa et al. | 455/68 | 6,294,896 B1 | 9/2001 | Champlin | 320/134 |
| 5,951,229 A | 9/1999 | Hammerslag | 414/398 | 6,294,897 B1 | 9/2001 | Champlin | 320/153 |
| 5,955,951 A | 9/1999 | Wischerop et al. | 340/572.8 | 6,304,087 B1 | 10/2001 | Bertness | 324/426 |
| 5,961,561 A | 10/1999 | Wakefield, II | 701/29 | 6,307,349 B1 | 10/2001 | Koenck et al. | 320/112 |
| 5,961,604 A | 10/1999 | Anderson et al. | 709/229 | 6,310,481 B2 | 10/2001 | Bertness | 324/430 |
| 5,969,625 A | 10/1999 | Russo | 340/636.19 | 6,313,607 B1 | 11/2001 | Champlin | 320/132 |
| 5,973,598 A | 10/1999 | Beigel | 340/572.1 | 6,313,608 B1 | 11/2001 | Varghese et al. | 320/132 |
| 5,978,805 A | 11/1999 | Carson | 707/10 | 6,316,914 B1 | 11/2001 | Bertness | 320/134 |
| 5,982,138 A | 11/1999 | Krieger | 320/105 | 6,320,351 B1 | 11/2001 | Ng et al. | 320/104 |
| 6,002,238 A | 12/1999 | Champlin | 320/134 | 6,323,650 B1 | 11/2001 | Bertness et al. | 324/426 |
| 6,005,489 A | 12/1999 | Siegle et al. | 340/825.69 | 6,329,793 B1 | 12/2001 | Bertness et al. | 320/132 |
| 6,005,759 A | 12/1999 | Hart et al. | 361/66 | 6,331,762 B1 | 12/2001 | Bertness | 320/134 |
| 6,008,652 A | 12/1999 | Theofanopoulos et al. | 324/434 | 6,332,113 B1 | 12/2001 | Bertness | 702/63 |
| 6,009,369 A | 12/1999 | Boisvert et al. | 701/99 | 6,346,795 B2 | 2/2002 | Haraguchi et al. | 320/136 |
| 6,016,047 A | 1/2000 | Notten et al. | 320/137 | 6,347,958 B1 | 2/2002 | Tsai | 439/488 |
| 6,031,354 A | 2/2000 | Wiley et al. | 320/116 | 6,351,102 B1 | 2/2002 | Troy | 320/139 |
| 6,031,368 A | 2/2000 | Klippel et al. | 324/133 | 6,356,042 B1 | 3/2002 | Kahlon et al. | 318/138 |
| 6,037,745 A | 3/2000 | Koike et al. | 320/104 | 6,359,441 B1 | 3/2002 | Bertness | 324/426 |
| 6,037,749 A | 3/2000 | Parsonage | 320/132 | 6,359,442 B1 | 3/2002 | Henningson et al. | 324/426 |
| 6,037,751 A | 3/2000 | Klang | 320/160 | 6,363,303 B1 | 3/2002 | Bertness | 701/29 |
| 6,037,777 A | 3/2000 | Champlin | 324/430 | RE37,677 E | 4/2002 | Irie | 315/83 |
| 6,037,778 A | 3/2000 | Makhija | 324/433 | 6,377,031 B1 | 4/2002 | Karuppana et al. | 323/220 |
| 6,046,514 A | 4/2000 | Rouillard et al. | 307/77 | 6,384,608 B1 | 5/2002 | Namaky | 324/430 |
| 6,051,976 A | 4/2000 | Bertness | 324/426 | 6,388,448 B1 | 5/2002 | Cervas | 324/426 |
| 6,055,468 A | 4/2000 | Kaman et al. | 701/29 | 6,392,414 B2 | 5/2002 | Bertness | 324/429 |
| 6,061,638 A | 5/2000 | Joyce | 702/63 | 6,396,278 B1 | 5/2002 | Makhija | 324/402 |
| 6,064,372 A | 5/2000 | Kahkoska | 345/173 | 6,407,554 B1 | 6/2002 | Godau et al. | 324/503 |
| 6,072,299 A | 6/2000 | Kurle et al. | 320/112 | 6,411,098 B1 | 6/2002 | Laletin | 324/436 |
| 6,072,300 A | 6/2000 | Tsuji | 320/116 | 6,417,669 B1 | 7/2002 | Champlin | 324/426 |
| 6,081,098 A | 6/2000 | Bertness et al. | 320/134 | 6,420,852 B1 | 7/2002 | Sato | 320/134 |
| 6,081,109 A | 6/2000 | Seymour et al. | 324/127 | 6,424,157 B1 | 7/2002 | Gollomp et al. | 324/430 |
| 6,087,815 A | 7/2000 | Pfeifer et al. | 323/282 | 6,424,158 B2 | 7/2002 | Klang | 324/433 |
| 6,091,238 A | 7/2000 | McDermott | 324/207.2 | 6,437,957 B1 | 8/2002 | Karuppana et al. | 361/78 |
| 6,091,245 A | 7/2000 | Bertness | 324/426 | 6,441,585 B1 | 8/2002 | Bertness | 320/132 |
| 6,094,033 A | 7/2000 | Ding et al. | 320/132 | 6,445,158 B1 | 9/2002 | Bertness et al. | 320/104 |
| 6,100,670 A | 8/2000 | Levesque | 320/150 | 6,449,726 B1 | 9/2002 | Smith | 713/340 |
| 6,104,167 A | 8/2000 | Bertness et al. | 320/132 | 6,456,036 B1 | 9/2002 | Thandiwe | 320/106 |
| 6,113,262 A | 9/2000 | Purola et al. | 374/45 | 6,456,045 B1 | 9/2002 | Troy et al. | 320/139 |
| 6,114,834 A | 9/2000 | Parise | 320/109 | 6,465,908 B1 | 10/2002 | Karuppana et al. | 307/31 |
| 6,137,269 A | 10/2000 | Champlin | 320/150 | 6,466,025 B1 | 10/2002 | Klang | 324/429 |
| 6,140,797 A | 10/2000 | Dunn | 320/105 | 6,466,026 B1 | 10/2002 | Champlin | 324/430 |
| 6,144,185 A | 11/2000 | Dougherty et al. | 320/132 | 6,469,511 B1 | 10/2002 | Vonderhaar et al. | 324/425 |
| 6,147,598 A | 11/2000 | Murphy et al. | 340/426.19 | 6,477,478 B1 | 11/2002 | Jones et al. | 702/102 |
| 6,150,793 A | 11/2000 | Lesesky et al. | 320/104 | 6,495,990 B2 | 12/2002 | Champlin | 320/132 |
| 6,158,000 A | 12/2000 | Collins | 713/1 | 6,497,209 B1 | 12/2002 | Karuppana et al. | 123/179.3 |
| 6,161,640 A | 12/2000 | Yamaguchi | 180/65.8 | 6,500,025 B1 | 12/2002 | Moenkhaus et al. | 439/502 |
| 6,163,156 A | 12/2000 | Bertness | 324/426 | 6,505,507 B1 | 1/2003 | Imao | 73/146.5 |
| 6,164,063 A | 12/2000 | Mendler | 60/274 | 6,507,196 B2 | 1/2003 | Thomsen et al. | 324/436 |
| 6,167,349 A | 12/2000 | Alvarez | 702/63 | 6,526,361 B1 | 2/2003 | Jones et al. | 702/63 |
| 6,172,483 B1 | 1/2001 | Champlin | 320/134 | 6,529,723 B1 | 3/2003 | Bentley | 455/405 |
| 6,172,505 B1 | 1/2001 | Bertness | 324/430 | 6,531,848 B1 | 3/2003 | Chitsazan et al. | 320/153 |
| 6,177,737 B1 | 1/2001 | Palfey et al. | 307/64 | 6,532,425 B1 | 3/2003 | Boost et al. | 702/63 |
| 6,181,545 B1 | 1/2001 | Amatucci et al. | 361/502 | 6,534,993 B2 | 3/2003 | Bertness | 324/433 |
| 6,211,651 B1 | 4/2001 | Nemoto | 320/133 | 6,536,536 B1 | 3/2003 | Gass et al. | 173/2 |
| 6,215,275 B1 | 4/2001 | Bean | 320/106 | 6,544,078 B2 | 4/2003 | Palmisano et al. | 439/762 |
| 6,218,936 B1 | 4/2001 | Imao | 340/447 | 6,545,599 B2 | 4/2003 | Derbyshire et al. | 340/442 |
| 6,222,342 B1 | 4/2001 | Eggert et al. | 320/105 | 6,556,019 B2 | 4/2003 | Bertness | 324/426 |
| 6,222,369 B1 | 4/2001 | Champlin | 324/430 | 6,566,883 B1 | 5/2003 | Vonderhaar et al. | 324/426 |
| D442,503 S | 5/2001 | Lundbeck et al. | D10/77 | 6,570,385 B1 | 5/2003 | Roberts et al. | 324/378 |
| 6,225,808 B1 | 5/2001 | Varghese et al. | 324/426 | 6,577,107 B2 | 6/2003 | Kechmire | 320/139 |
| 6,236,332 B1 | 5/2001 | Conkright et al. | 340/3.1 | 6,586,941 B2 | 7/2003 | Bertness et al. | 324/426 |
| 6,238,253 B1 | 5/2001 | Qualls | 439/759 | 6,597,150 B1 | 7/2003 | Bertness et al. | 320/104 |
| 6,242,887 B1 | 6/2001 | Burke | 320/104 | 6,599,243 B2 | 7/2003 | Woltermann et al. | 600/300 |
| 6,249,124 B1 | 6/2001 | Bertness | 324/426 | 6,600,815 B1 | 7/2003 | Walding | 379/93.07 |
| 6,250,973 B1 | 6/2001 | Lowery et al. | 439/763 | 6,611,740 B2 | 8/2003 | Lowrey et al. | 701/29 |
| 6,254,438 B1 | 7/2001 | Gaunt | 439/755 | 6,614,349 B1 | 9/2003 | Proctor et al. | 340/572.1 |
| 6,259,170 B1 | 7/2001 | Limoge et al. | 307/10.8 | 6,618,644 B2 | 9/2003 | Bean | 700/231 |
| 6,259,254 B1 | 7/2001 | Klang | 324/427 | 6,621,272 B2 | 9/2003 | Champlin | 324/426 |
| 6,262,563 B1 | 7/2001 | Champlin | 320/134 | 6,623,314 B1 | 9/2003 | Cox et al. | 439/759 |
| 6,263,268 B1 | 7/2001 | Nathanson | 701/29 | 6,624,635 B1 | 9/2003 | Lui | 324/426 |

| | | | | | | |
|---|---|---|---|---|---|---|
| 6,628,011 B2 | 9/2003 | Droppo et al. ............... 307/43 | 2003/0025481 A1 | 2/2003 | Bertness .................... 324/427 |
| 6,629,054 B2 | 9/2003 | Makhija et al. ............ 702/113 | 2003/0036909 A1 | 2/2003 | Kato ........................ 704/275 |
| 6,633,165 B2 | 10/2003 | Bertness .................... 324/426 | 2003/0040873 A1 | 2/2003 | Lesesky et al. ............ 702/57 |
| 6,635,974 B1 | 10/2003 | Karuppana et al. ......... 307/140 | 2003/0088375 A1 | 5/2003 | Bertness et al. ............ 702/63 |
| 6,667,624 B1 | 12/2003 | Raichle et al. ............ 324/522 | 2003/0137277 A1 | 7/2003 | Mori et al. ................. 320/132 |
| 6,679,212 B2 | 1/2004 | Kelling ................ 123/179.28 | 2003/0169018 A1 | 9/2003 | Berels et al. ............... 320/132 |
| 6,686,542 B2 | 2/2004 | Zhang ....................... 174/74 | 2003/0184262 A1 | 10/2003 | Makhija .................... 320/156 |
| 6,696,819 B2 | 2/2004 | Bertness .................... 320/134 | 2003/0184306 A1 | 10/2003 | Bertness et al. ............ 324/426 |
| 6,707,303 B2 | 3/2004 | Bertness et al. ............ 324/426 | 2003/0187556 A1 | 10/2003 | Suzuki ...................... 701/29 |
| 6,736,941 B2 | 5/2004 | Oku et al. ................... 203/68 | 2003/0194672 A1 | 10/2003 | Roberts et al. ............. 431/196 |
| 6,737,831 B2 | 5/2004 | Champlin .................. 320/132 | 2003/0214395 A1 | 11/2003 | Flowerday et al. ......... 340/445 |
| 6,738,697 B2 | 5/2004 | Breed ........................ 701/29 | 2004/0000590 A1 | 1/2004 | Raichle et al. ......... 235/462.01 |
| 6,740,990 B2 | 5/2004 | Tozuka et al. ............... 307/9.1 | 2004/0000891 A1 | 1/2004 | Raichle et al. ............ 320/107 |
| 6,744,149 B1 | 6/2004 | Karuppana et al. ........... 307/31 | 2004/0000893 A1 | 1/2004 | Raichle et al. ............ 320/135 |
| 6,745,153 B2 | 6/2004 | White et al. ............... 702/184 | 2004/0002824 A1 | 1/2004 | Raichle et al. .............. 702/63 |
| 6,759,849 B2 | 7/2004 | Bertness .................... 324/426 | 2004/0002825 A1 | 1/2004 | Raichle et al. .............. 702/63 |
| 6,777,945 B2 | 8/2004 | Roberts et al. ............. 324/426 | 2004/0002836 A1 | 1/2004 | Raichle et al. ............ 702/188 |
| 6,781,382 B2 | 8/2004 | Johnson .................... 324/426 | 2004/0032264 A1 | 2/2004 | Schoch ..................... 324/426 |
| 6,784,635 B2 | 8/2004 | Larson ...................... 320/104 | 2004/0044452 A1 | 3/2004 | Bauer et al. .................. 703/33 |
| 6,784,637 B2 | 8/2004 | Raichle et al. ............ 320/107 | 2004/0049361 A1 | 3/2004 | Hamdan et al. ............ 702/115 |
| 6,788,025 B2 | 9/2004 | Bertness et al. ............ 320/104 | 2004/0051533 A1 | 3/2004 | Namaky .................... 324/426 |
| 6,795,782 B2 | 9/2004 | Bertness et al. ............ 702/63 | 2004/0054503 A1 | 3/2004 | Namaky .................... 702/182 |
| 6,796,841 B1 | 9/2004 | Cheng et al. .............. 439/620.3 | 2004/0113588 A1 | 6/2004 | Mikuriya et al. ............ 320/128 |
| 6,805,090 B2 | 10/2004 | Bertness et al. ............ 123/198 | 2004/0145342 A1 | 7/2004 | Lyon ........................ 320/108 |
| 6,806,716 B2 | 10/2004 | Bertness et al. ............ 324/426 | 2004/0178185 A1 | 9/2004 | Yoshikawa et al. ......... 219/270 |
| 6,825,669 B2 | 11/2004 | Raichle et al. ............ 324/426 | 2004/0227523 A1 | 11/2004 | Namaky .................... 324/537 |
| 6,842,707 B2 | 1/2005 | Raichle et al. .............. 702/62 | 2004/0239332 A1 | 12/2004 | Mackel et al. .............. 324/426 |
| 6,845,279 B1 | 1/2005 | Gilmore et al. ............. 700/115 | 2005/0017726 A1 | 1/2005 | Koran et al. ............... 324/433 |
| 6,850,037 B2 | 2/2005 | Bertness .................... 320/132 | 2005/0025299 A1 | 2/2005 | Tischer et al. .............. 379/199 |
| 6,871,151 B2 | 3/2005 | Bertness .................... 702/63 | 2005/0043868 A1 | 2/2005 | Mitcham .................... 701/29 |
| 6,885,195 B2 | 4/2005 | Bertness .................... 324/426 | 2005/0057256 A1 | 3/2005 | Bertness .................... 324/426 |
| 6,888,468 B2 | 5/2005 | Bertness ................ 340/636.15 | 2005/0102073 A1 | 5/2005 | Ingram ...................... 701/29 |
| 6,891,378 B2 | 5/2005 | Bertness et al. ............ 324/426 | 2005/0182536 A1 | 8/2005 | Doyle et al. ................. 701/29 |
| 6,904,796 B2 | 6/2005 | Pacsai et al. ............... 73/146.8 | 2005/0254106 A9 | 11/2005 | Silverbrook et al. ........ 358/539 |
| 6,906,522 B2 | 6/2005 | Bertness et al. ............ 324/426 | 2005/0256617 A1 | 11/2005 | Cawthorne et al. ........... 701/22 |
| 6,906,523 B2 | 6/2005 | Bertness et al. ............ 324/426 | 2006/0030980 A1 | 2/2006 | St. Denis .................... 701/29 |
| 6,906,624 B2 | 6/2005 | McClelland et al. ........ 340/442 | 2006/0089767 A1 | 4/2006 | Sowa ......................... 701/29 |
| 6,909,287 B2 | 6/2005 | Bertness .................... 324/427 | 2006/0217914 A1 | 9/2006 | Bertness .................... 702/113 |
| 6,909,356 B2 | 6/2005 | Brown et al. ............... 340/3.2 | | | |
| 6,913,483 B2 | 7/2005 | Restaino et al. ............. 439/504 | | FOREIGN PATENT DOCUMENTS | |
| 6,914,413 B2 | 7/2005 | Bertness et al. ............ 320/104 | DE | 196 38 324 | 9/1996 |
| 6,919,725 B2 | 7/2005 | Bertness et al. ............ 324/433 | EP | 0 022 450 A1 | 1/1981 |
| 6,930,485 B2 | 8/2005 | Bertness et al. ............ 324/426 | EP | 0 637 754 A1 | 2/1995 |
| 6,933,727 B2 | 8/2005 | Bertness et al. ............ 324/426 | EP | 0 772 056 A1 | 5/1997 |
| 6,941,234 B2 | 9/2005 | Bertness et al. ............ 702/63 | EP | 0 982 159 A2 | 3/2000 |
| 6,967,484 B2 | 11/2005 | Bertness .................... 324/426 | FR | 2 749 397 | 12/1997 |
| 6,972,662 B1 | 12/2005 | Ohkawa et al. ............ 340/10.1 | GB | 2 029 586 | 3/1980 |
| 6,998,847 B2 | 2/2006 | Bertness et al. ............ 324/426 | GB | 2 088 159 A | 6/1982 |
| 7,003,410 B2 | 2/2006 | Bertness et al. ............ 702/63 | GB | 2 246 916 A | 10/1990 |
| 7,003,411 B2 | 2/2006 | Bertness .................... 702/63 | GB | 2 275 783 A | 7/1994 |
| 7,012,433 B2 | 3/2006 | Smith et al. ................ 324/426 | GB | 2 387 235 A | 10/2003 |
| 7,058,525 B2 | 6/2006 | Bertness et al. ............ 702/63 | JP | 59-17892 | 1/1984 |
| 7,081,755 B2 | 7/2006 | Klang et al. ................ 324/426 | JP | 59-17893 | 1/1984 |
| 7,106,070 B2 | 9/2006 | Bertness et al. ............ 324/538 | JP | 59017894 | 1/1984 |
| 7,116,109 B2 | 10/2006 | Klang ........................ 324/426 | JP | 59215674 | 12/1984 |
| 7,119,686 B2 | 10/2006 | Bertness et al. .......... 340/572.1 | JP | 60225078 | 11/1985 |
| 7,120,488 B2 | 10/2006 | Nova et al. ..................... 600/2 | JP | 62-180284 | 8/1987 |
| 7,126,341 B2 | 10/2006 | Bertness et al. ............ 324/426 | JP | 63027776 | 2/1988 |
| 7,129,706 B2 | 10/2006 | Kalley ........................ 324/426 | JP | 03274479 | 12/1991 |
| 7,182,147 B2 | 2/2007 | Cutler et al. ................. 173/1 | JP | 03282276 | 12/1991 |
| 7,200,424 B2 | 4/2007 | Tischer et al. .............. 455/567 | JP | 4-8636 | 1/1992 |
| 7,209,860 B2 | 4/2007 | Trsar et al. .................. 702/183 | JP | 04095788 | 3/1992 |
| 7,212,887 B2 | 5/2007 | Shah et al .................. 700/276 | JP | 04131779 | 5/1992 |
| 7,272,519 B2 | 9/2007 | Lesesky et al. ............. 702/63 | JP | 04372536 | 12/1992 |
| 7,339,477 B2 | 3/2008 | Puzio et al. ............. 340/572.1 | JP | 05211724 A | 8/1993 |
| 7,446,536 B2 * | 11/2008 | Bertness .................... 324/426 | JP | 5216550 | 8/1993 |
| 2002/0004694 A1 | 1/2002 | Mcleod ........................ 701/29 | JP | 7-128414 | 5/1995 |
| 2002/0010558 A1 | 1/2002 | Bertness et al. ............ 702/63 | JP | 09061505 | 3/1997 |
| 2002/0041175 A1 | 4/2002 | Lauper et al. ............... 320/106 | JP | 10056744 | 2/1998 |
| 2002/0044050 A1 | 4/2002 | Derbyshire et al. ......... 340/442 | JP | 10232273 | 9/1998 |
| 2002/0171428 A1 | 11/2002 | Bertness .................... 702/63 | JP | 11103503 A | 4/1999 |
| 2002/0176010 A1 | 11/2002 | Wallach et al. ............. 348/362 | RU | 2089015 C1 | 8/1997 |
| 2003/0009270 A1 | 1/2003 | Breed ........................ 701/29 | | | |

| | | |
|---|---|---|
| WO | WO 93/22666 | 11/1993 |
| WO | WO 94/05069 | 3/1994 |
| WO | WO 96/01456 | 1/1996 |
| WO | WO 96/06747 | 3/1996 |
| WO | WO 97/01103 | 1/1997 |
| WO | WO 97/44652 | 11/1997 |
| WO | WO 98/04910 | 2/1998 |
| WO | WO 98/58270 | 12/1998 |
| WO | WO 99/23738 | 5/1999 |
| WO | WO 00/16083 | 3/2000 |
| WO | WO 00/62049 | 10/2000 |
| WO | WO 00/67359 | 11/2000 |
| WO | WO 01/59443 | 2/2001 |
| WO | WO 01/16614 | 3/2001 |
| WO | WO 01/16615 | 3/2001 |
| WO | WO 01/51947 | 7/2001 |
| WO | WO 03/047064 A3 | 6/2003 |
| WO | WO 03/076960 A1 | 9/2003 |
| WO | WO 2004/047215 A1 | 6/2004 |

OTHER PUBLICATIONS

"Battery Impedance", by E. Willihnganz et al., *Electrical Engineering*, Sep. 1959, pp. 922-925.
"Determining the End of Battery Life", by S. DeBardelaben, *IEEE*, 1986, pp. 365-368.
"A Look at the Impedance of a Cell", by S. Debardelaben, *IEEE*, 1988, pp. 394-397.
"The Impedance of Electrical Storage Cells", by N. A. Hampson et al., *Journal of Applied Electrochemistry*, 1980, pp. 3-11.
"A Package for Impedance/Admittance Data Analysis", by B. Boukamp, *Solid State Ionics*, 1986, pp. 136-140.
"Precision of Impedance Spectroscopy Estimates of Bulk, Reaction Rate, and Diffusion Parameters", by J. Macdonald et al., *J. Electroanal, Chem.*, 1991, pp. 1-11.
Internal Resistance: Harbinger of Capacity Loss in Starved Electrolyte Sealed Lead Acid Batteries, by Vaccaro, F.J. et al., *AT&T Bell Laboratories*, 1987 IEEE, Ch. 2477, pp. 128,131.
IEEE Recommended Practice for Maintenance, Testings, and Replacement of Large Lead Storage Batteries for Generating Stations and Substations, *The Institute of Electrical and Electronics Engineers, Inc., ANSI/IEEE Std.* 450-1987, Mar. 9, 1987, pp. 7-15.
"Field and Laboratory Studies to Assess the State of Health of Valve-Regulated Lead Acid Batteries: Part I Conductance/Capacity Correlation Studies", by D. Feder et al., *IEEE*, Aug. 1992, pp. 218-233.
"JIS Japanese Industrial Standard-Lead Acid Batteries for Automobiles", *Japanese Standards Association UDC*, 621.355.2:629.113.006, Nov. 1995.
"Performance of Dry Cells", by C. Hambuechen, Preprint of *Am. Electrochem. Soc.*, Apr. 18-20, 1912, paper No. 19, pp. 1-5.
"A Bridge for Measuring Storage Battery Resistance", by E. Willihncanz, *The Electrochemical Society*, preprint 79-20, Apr. 1941, pp. 253-258.
National Semiconductor Corporation, "High Q Notch Filter", Linear Brief 5, Mar. 1969.
Burr-Brown Corporation, "Design A 60 Hz Notch Filter with the UAF42", Jan. 1994, AB-071.
National Semiconductor Corporation, "LMF90-4$^{th}$-Order Elliptic Notch Filter", RRD-B30M115, Dec. 1994.
"Alligator Clips with Wire Penetrators" *J.S. Popper, Inc.* product information, downloaded from http://www.jspopper.com/, prior to Oct. 1, 2002.
"#12: LM78S40 Simple Switcher DC to DC Converter", *ITM e-Catalog*, downloaded from http://www.pcbcafe.com, prior to Oct. 1, 2002.
"Simple DC-DC Converts Allows Use of Single Battery", *Electronix Express*, downloaded from http://www.elexp.com/t_dc-dc.htm, prior to Oct. 1, 2002.
"DC-DC Converter Basics", *Power Designers*, downloaded from http://www.powederdesigners.com/InforWeb.design_center/articles/DC-DC/converter.shtm, prior to Oct. 1, 2002.
"Notification of Transmittal of the International Search Report or the Declaration", PCT/US02/29461, Jan. 2003.
"Notification of Transmittal of the International Search Report or the Declaration", PCT/US03/07546, Jul. 2003.
"Notification of Transmittal of the International Search Report or the Declaration", PCT/US03/06577, Jul. 2003.
"Notification of Transmittal of the International Search Report or the Declaration", PCT/US03/07837, Jul. 2003.
"Improved Impedance Spectroscopy Technique for Status Determination of Production Li/SO$_2$ Batteries" Terrill Atwater et al., pp. 10-113, (1992).
"Notification of Transmittal of the International Search Report or the Declaration", PCT/US03/41561, May 2004.
"Notification of Transmittal of the International Search Report or the Declaration", PCT/US03/27696, Apr. 2004.
"Programming Training Course, 62-000 Series Smart Engine Analyzer", Testproducts Division, Kalamazoo, Michigan, pp. 1-207, (1984).
"Operators Manual; Modular Computer Analyzer Model MCA 3000", Sun Electric Corporation, Crystal Lake, Illinois, pp. 1-1-14-13, (1991).
Supplementary European Search Report Communication for Appl. No. 99917402.2; Sep. 7, 2004.
"Dynamic modelling of lead/acid batteries using impedance, spectroscopy for parameter identification", Journal of Power Sources, pp. 69-84, (1997).
Notification of Transmittal of the International Search Report for PCT/US03/30707, Nov. 2004.
"A review of impedance measurements for determination of the state-of-charge or state-of-health of secondary batteries", Journal of Power Sources; pp. 59-69, (1998).
"Search Report Under Section 17" for Great Britain Application No. GB0421447.4.
"Results of Discrete Frequency Immittance Spectroscopy (DFIS) Measurements of Lead Acid Batteries", by K.S. Champlin et al., *Proceedings of 23$^{rd}$ International Teleco Conference (INTELEC)*, published Oct. 2001, IEE, pp. 433-440.
"Examination Report" from the UK Patent Office for App. No. 0417678.0; Jan. 24, 2005.
Wikipedia Online Encyclopedia, Inductance, 2005, http://en.wikipedia.org/wiki/inductance, pp. 1-5, mutual Inductance, pp. 3,4.
"Professional BCS System Analyzer Battery-Charger-Starting", pp. 2-8, (2001).
Young Illustrated Encyclopedia Dictionary of Electronics, 1981, Parker Publishing Company, Inc., pp. 318-319.
Office Action from U.S. Appl. No. 11/352,945; dated Jan. 5, 2007.
Office Action from U.S. Appl. No. 11/146,608 dated May 13, 2008.
Office Action from U.S. Appl. No. 11/063,247 dated Apr. 11, 2008.
"DSP Applications in Hybrid Electric Vehicle Powertrain", Miller et al., Proceedings of the American Control Conference, Sand Diego, CA, Jun. 1999; 2 ppg.
"Notification of Transmittal of the International Search Report and the Written Opinion of the International Searching Authority, or the Declaration" for PCT/US2008/008702 filed Jul. 2008; 15 pages.
"Notification Concerning Availability of the Publication of the International Application" for PCT/US2008/008702, filed Jul. 17, 2008; 24 pages.
"A Microprocessor-Based Control System for a Near-Term Electric Vehicle", Bimal K. Bose; IEEE Transactions on Industry Applications, vol. IA-17, No. 6, Nov./Dec. 198?,; 0093-9994/81/1100-0626$00.75 © 1981 IEEE, 6 pages.
"First Notice Informing the Applicant of the Communication of the International Application (To Designated Offices which do not apply the 30 Month Time Limit Under Article 22(1))" for PCT/US2008/008702 filed Jul. 17, 2008; one page.
"Notification of the Recording of a Change" for PCT/US2008/008702 filed Jul. 17, 2008; one page.

* cited by examiner

ELECTRONIC BATTERY TESTER WITH DATABUS

The present application is a Continuation of U.S. Ser. No. 10/958,812, filed Oct. 5, 2004, which is a Continuation-In-Part of U.S. Ser. No. 10/460,749, filed Jun. 12, 2003, which is a Continuation-In-Part of U.S. Ser. No. 10/280,186, filed Oct. 25, 2002, now U.S. Pat. No. 6,759,849, the present application is also a Continuation-In-Part of U.S. patent application Ser. No. 09/816,768, filed Mar. 23, 2001, now U.S. Pat. No. 6,586,941, which claims the benefit of U.S. provisional patent application Ser. No. 60/192,222, filed Mar. 27, 2000, the contents of which are hereby incorporated by reference in their entirety.

BACKGROUND OF THE INVENTION

The present invention relates to battery testers of the type used to test storage batteries. More specifically, the present invention relates to a modular battery tester capable of interfacing with other types of test equipment.

Various types of battery testers are known in the art. One type of battery tester is based upon the measurement of a dynamic parameter, such as dynamic conductance. Examples of various battery testers and monitors are forth in U.S. Pat. No. 3,873,911, issued Mar. 25, 1975, to Champlin; U.S. Pat. No. 3,909,708, issued Sep. 30, 1975, to Champlin; U.S. Pat. No. 4,816,768, issued Mar. 28, 1989, to Champlin; U.S. Pat. No. 4,825,170, issued Apr. 25, 1989, to Champlin; U.S. Pat. No. 4,881,038, issued Nov. 14, 1989, to Champlin; U.S. Pat. No. 4,912,416, issued Mar. 27, 1990, to Champlin; U.S. Pat. No. 5,140,269, issued Aug. 18, 1992, to Champlin; U.S. Pat. No. 5,343,380, issued Aug. 30, 1994; U.S. Pat. No. 5,572,136, issued Nov. 5, 1996; U.S. Pat. No. 5,574,355, issued Nov. 12, 1996; U.S. Pat. No. 5,583,416, issued Dec. 10, 1996; U.S. Pat. No. 5,585,728, issued Dec. 17, 1996; U.S. Pat. No. 5,589,757, issued Dec. 31, 1996; U.S. Pat. No. 5,592,093, issued Jan. 7, 1997; U.S. Pat. No. 5,598,098, issued Jan. 28, 1997; U.S. Pat. No. 5,656,920, issued Aug. 12, 1997; U.S. Pat. No. 5,757,192, issued May 26, 1998; U.S. Pat. No. 5,821,756, issued Oct. 13, 1998; U.S. Pat. No. 5,831,435, issued Nov. 3, 1998; U.S. Pat. No. 5,871,858, issued Feb. 16, 1999; U.S. Pat. No. 5,914,605, issued Jun. 22, 1999; U.S. Pat. No. 5,945,829, issued Aug. 31, 1999; U.S. Pat. No. 6,002,238, issued Dec. 14, 1999; U.S. Pat. No. 6,037,751, issued Mar. 14, 2000; U.S. Pat. No. 6,037,777, issued Mar. 14, 2000; U.S. Pat. No. 6,051,976, issued Apr. 18, 2000; U.S. Pat. No. 6,081,098, issued Jun. 27, 2000; U.S. Pat. No. 6,091,245, issued Jul. 18, 2000; U.S. Pat. No. 6,104,167, issued Aug. 15, 2000; U.S. Pat. No. 6,137,269, issued Oct. 24, 2000; U.S. Pat. No. 6,163,156, issued Dec. 19, 2000; U.S. Pat. No. 6,172,483, issued Jan. 9, 2001; U.S. Pat. No. 6,172,505, issued Jan. 9, 2001; U.S. Pat. No. 6,222,369, issued Apr. 24, 2001; U.S. Pat. No. 6,225,808, issued May 1, 2001; U.S. Pat. No. 6,249,124, issued Jun. 19, 2001; U.S. Pat. No. 6,259,254, issued Jul. 10, 2001; U.S. Pat. No. 6,262,563, issued Jul. 17, 2001; U.S. Pat. No. 6,294,896, issued Sep. 25, 2001; U.S. Pat. No. 6,294,897, issued Sep. 25, 2001; U.S. Pat. No. 6,304,087, issued Oct. 16, 2001; U.S. Pat. No. 6,310,481, issued Oct. 30, 2001; U.S. Pat. No. 6,313,607, issued Nov. 6, 2001; U.S. Pat. No. 6,313,608, issued Nov. 6, 2001; U.S. Pat. No. 6,316,914, issued Nov. 13, 2001; U.S. Pat. No. 6,323,650, issued Nov. 27, 2001; U.S. Pat. No. 6,329,793, issued Dec. 11, 2001; U.S. Pat. No. 6,331,762, issued Dec. 18, 2001; U.S. Pat. No. 6,332,113, issued Dec. 18, 2001; U.S. Pat. No. 6,351,102, issued Feb. 26, 2002; U.S. Pat. No. 6,359,441, issued Mar. 19, 2002; U.S. Pat. No. 6,363,303, issued Mar. 26, 2002; U.S. Pat. No. 6,377,031, issued Apr. 23, 2002; U.S. Pat. No. 6,392,414, issued May 21, 2002; U.S. Pat. No. 6,417,669, issued Jul. 9, 2002; U.S. Pat. No. 6,424,158, issued Jul. 23, 2002; U.S. Pat. No. 6,441,585, issued Aug. 17, 2002; U.S. Pat. No. 6,437,957, issued Aug. 20, 2002; U.S. Pat. No. 6,445,158, issued Sep. 3, 2002; U.S. Pat. No. 6,456,045; U.S. Pat. No. 6,466,025, issued Oct. 15, 2002; U.S. Pat. No. 6,465,908, issued Oct. 15, 2002; U.S. Pat. No. 6,466,026, issued Oct. 15, 2002; U.S. Pat. No. 6,469,511, issued Nov. 22, 2002; U.S. Pat. No. 6,495,990, issued Dec. 17, 2002; U.S. Pat. No. 6,497,209, issued Dec. 24, 2002; U.S. Pat. No. 6,507,196, issued Jan. 14, 2003; U.S. Pat. No. 6,534,993; issued Mar. 18, 2003; U.S. Pat. No. 6,544,078, issued Apr. 8, 2003; U.S. Pat. No. 6,556,019, issued Apr. 29, 2003; U.S. Pat. No. 6,566,883, issued May 20, 2003; U.S. Pat. No. 6,586,941, issued Jul. 1, 2003; U.S. Pat. No. 6,597,150, issued Jul. 22, 2003; U.S. Pat. No. 6,621,272, issued Sep. 16, 2003; U.S. Pat. No. 6,623,314, issued Sep. 23, 2003; U.S. Pat. No. 6,633,165, issued Oct. 14, 2003; U.S. Pat. No. 6,635,974, issued Oct. 21, 2003; U.S. Pat. No. 6,707,303, issued Mar. 16, 2004; U.S. Pat. No. 6,737,831, issued May 18, 2004; U.S. Pat. No. 6,744,149, issued Jun. 1, 2004; U.S. Pat. No. 6,759,849, issued Jul. 6, 2004; U.S. Pat. No. 6,781,382, issued Aug. 24, 2004; U.S. Pat. No. 6,788,025, filed Sep. 7, 2004; U.S. Pat. No. 6,795,782, issued Sep. 21, 2004; U.S. Pat. No. 6,805,090, filed Oct. 19, 2004; U.S. Pat. No. 6,806,716, filed Oct. 19, 2004; U.S. Pat. No. 6,850,037, filed Feb. 1, 2005; U.S. Pat. No. 6,850,037, issued Feb. 1, 2005; U.S. Pat. No. 6,871,151, issued Mar. 22, 2005; U.S. Pat. No. 6,885,195, issued Apr. 26, 2005; U.S. Pat. No. 6,888,468, issued May 3, 2005; U.S. Pat. No. 6,891,378, issued May 10, 2005; U.S. Pat. No. 6,906,522, issued Jun. 14, 2005; U.S. Pat. No. 6,906,523, issued Jun. 14, 2005; U.S. Pat. No. 6,909,287, issued Jun. 21, 2005; U.S. Pat. No. 6,914,413, issued Jul. 5, 2005; U.S. Pat. No. 6,913,483, issued Jul. 5, 2005; U.S. Pat. No. 6,930,485, issued Aug. 16, 2005; U.S. Pat. No. 6,933,727, issued Aug. 23, 200; U.S. Pat. No. 6,941,234, filed Sep. 6, 2005; U.S. Pat. No. 6,967,484, issued Nov. 22, 2005; U.S. Pat. No. 6,998,847, issued Feb. 14, 2006; U.S. Pat. No. 7,003,410, issued Feb. 21, 2006; U.S. Pat. No. 7,003,411, issued Feb. 21, 2006; U.S. Pat. No. 7,012,433, issued Mar. 14, 2006; U.S. Pat. No. 7,015,674, issued Mar. 21, 2006; U.S. Pat. No. 7,034,541, issued Apr. 25, 2006; U.S. Pat. No. 7,039,533, issued May 2, 2006; U.S. Pat. No. 7,058,525, issued Jun. 6, 2006; U.S. Pat. No. 7,081,755, issued Jul. 25, 2006; U.S. Pat. No. 7,106,070, issued Sep. 12, 2006; U.S. Pat. No. 7,116,109, issued Oct. 3, 2006; U.S. Pat. No. 7,119,686, issued Oct. 10, 2006; and U.S. Pat. No. 7,126,341, issued Oct. 24, 2006; U.S. Pat. No. 7,154,276, issued Dec. 26, 2006; U.S. Pat. No. 7,198,510, issued Apr. 3, 2007; U.S. Pat. No. 7,363,175, issued Apr. 22, 2008; U.S. Pat. No. 7,208,914, issued Apr. 24, 2007; U.S. Pat. No. 7,246,015, issued Jul. 17, 2007; U.S. Pat. No. 7,295,936, issued Nov. 13, 2007; U.S. Pat. No. 7,319,304, issued Jan. 15, 2008; U.S. Pat. No. 7,363,175, issued Apr. 22, 2008; U.S. Pat. No. 7,398,176, issued Jul. 8, 2008; U.S. Pat. No. 7,408,358, issued Aug. 5, 2008; U.S. Ser. No. 09/780,146, filed Feb. 9, 2001, entitled STORAGE BATTERY WITH INTEGRAL BATTERY TESTER; U.S. Ser. No. 09/756,638, filed Jan. 8, 2001, entitled METHOD AND APPARATUS FOR DETERMINING BATTERY PROPERTIES FROM COMPLEX IMPEDANCE/ADMITTANCE; U.S. Ser. No. 09/862,783, filed May 21, 2001, entitled METHOD AND APPARATUS FOR TESTING CELLS AND BATTERIES EMBEDDED IN SERIES/PARALLEL SYSTEMS; U.S. Ser. No. 09/880,473, filed Jun. 13, 2001; entitled BATTERY TEST MODULE; U.S. Ser. No. 10/042,451, filed Jan. 8, 2002, entitled BATTERY CHARGE CONTROL DEVICE; U.S. Ser. No. 10/109,734, filed Mar. 28, 2002, entitled APPARATUS AND METHOD FOR COUN- TERACTING SELF DISCHARGE IN A STORAGE BATTERY; U.S. Ser. No. 10/112,998, filed Mar. 29, 2002, entitled BATTERY TESTER WITH BATTERY REPLACEMENT OUTPUT; U.S. Ser. No. 10/263,473, filed Oct. 2, 2002, entitled ELECTRONIC BATTERY TESTER WITH RELATIVE TEST OUTPUT; U.S. Ser. No. 10/310,385, filed Dec. 5, 2002, entitled BATTERY TEST MODULE; U.S. Ser. No. 10/653,342, filed Sep. 2, 2003, entitled ELECTRONIC BATTERY TESTER CONFIGURED TO PREDICT A LOAD TEST RESULT; U.S. Ser. No. 10/441,271, filed May 19, 2003, entitled ELECTRONIC BATTERY TESTER; U.S. Ser. No. 09/653,963, filed Sep. 1, 2000, entitled SYSTEM AND METHOD FOR CONTROLLING POWER GENERATION AND STORAGE; U.S. Ser. No. 10/174,110, filed Jun. 18, 2002, entitled DAYTIME RUNNING LIGHT CONTROL USING AN INTELLIGENT POWER MANAGEMENT SYSTEM; U.S. Ser. No. 10/258,441, filed Apr. 9, 2003, entitled CURRENT MEASURING CIRCUIT SUITED FOR BATTERIES; U.S. Ser. No. 10/681,666, filed Oct. 8, 2003, entitled ELECTRONIC BATTERY TESTER WITH PROBE LIGHT; U.S. Ser. No. 10/783,682, filed Feb. 20, 2004, entitled REPLACEABLE CLAMP FOR ELECTRONIC BATTERY TESTER; U.S. Ser. No. 10/791,141, filed Mar. 2, 2004, entitled METHOD AND APPARATUS FOR AUDITING A BATTERY TEST; U.S. Ser. No. 10/867,385, filed Jun. 14, 2004, entitled ENERGY MANAGEMENT SYSTEM FOR AUTOMOTIVE VEHICLE; U.S. Ser. No. 10/896,834, filed Jul. 22, 2004, entitled ELECTRONIC BATTERY TESTER; U.S. Ser. No. 10/958,821, filed Oct. 5, 2004, entitled IN-VEHICLE BATTERY MONITOR; U.S. Ser. No. 10/958,812, filed Oct. 5, 2004, entitled SCAN TOOL FOR ELECTRONIC BATTERY TESTER; U.S. Ser. No. 11/008,456, filed Dec. 9, 2004, entitled APPARATUS AND METHOD FOR PREDICTING BATTERY CAPACITY AND FITNESS FOR SERVICE FROM A BATTERY DYNAMIC PARAMETER AND A RECOVERY VOLTAGE DIFFERENTIAL, U.S. Ser. No. 60/587,232, filed Dec. 14, 2004, entitled CELLTRON ULTRA, U.S. Ser. No. 11/018,785, filed Dec. 21, 2004, entitled WIRELESS BATTERY MONITOR; U.S. Ser. No. 60/653,537, filed Feb. 16, 2005, entitled CUSTOMER MANAGED WARRANTY CODE; U.S. Ser. No. 11/063,247, filed Feb. 22, 2005, entitled ELECTRONIC BATTERY TESTER OR CHARGER WITH DATABUS CONNECTION; U.S. Ser. No. 60/665,070, filed Mar. 24, 2005, entitled OHMMETER PROTECTION CIRCUIT; U.S. Ser. No. 11/141,234, filed May 31, 2005, entitled BATTERY TESTER CAPABLE OF IDENTIFYING FAULTY BATTERY POST ADAPTERS; U.S. Ser. No. 11/143,828, filed Jun. 2, 2005, entitled BATTERY TEST MODULE; U.S. Ser. No. 11/146,608, filed Jun. 7, 2005, entitled SCAN TOOL FOR ELECTRONIC BATTERY TESTER; U.S. Ser. No. 60,694,199, filed Jun. 27, 2005, entitled GEL BATTERY CONDUCTANCE COMPENSATION; U.S. Ser. No. 11/178,550, filed Jul. 11, 2005, entitled WIRELESS BATTERY TESTER/CHARGER; U.S. Ser. No. 60/705,389, filed Aug. 4, 2005, entitled PORTABLE TOOL THEFT PREVENTION SYSTEM, U.S. Ser. No. 11/207,419, filed Aug. 19, 2005, entitled SYSTEM FOR AUTOMATICALLY GATHERING BATTERY INFORMATION FOR USE DURING BATTERY TESTER/CHARGING, U.S. Ser. No. 60/712,322, filed Aug. 29, 2005, entitled AUTOMOTIVE VEHICLE ELECTRICAL SYSTEM DIAGNOSTIC DEVICE, U.S. Ser. No. 60/713,168, filed Aug. 31, 2005, entitled LOAD TESTER SIMULATION WITH DISCHARGE COMPENSATION, U.S. Ser. No. 60/731,881, filed Oct. 31, 2005, entitled PLUG-IN FEATURES FOR BATTERY TESTERS; U.S. Ser. No. 60/731,887, filed Oct. 31, 2005, entitled AUTOMOTIVE VEHICLE ELECTRICAL SYSTEM DIAGNOSTIC DEVICE; U.S. Ser. No. 11/304,004, filed Dec. 14, 2005, entitled BATTERY TESTER THAT CALCULATES ITS OWN REFERENCE VALUES; U.S. Ser. No. 60/751,853, filed Dec. 20, 2005, entitled BATTERY MONITORING SYSTEM; U.S. Ser. No. 11/304,004, filed Dec. 14, 2005, entitled BATTERY TESTER WITH CALCULATES ITS OWN REFERENCE VALUES; U.S. Ser. No. 60/751,853, filed Dec. 20, 2005, entitled BATTERY MONITORING SYSTEM; U.S. Ser. No. 11/356,299, filed Feb. 16, 2006, entitled CENTRALLY MONITORED SALES OF STORAGE BATTERIES; U.S. Ser. No. 11/356,443, filed Feb. 16, 2006, entitled ELECTRONIC BATTERY TESTER WITH NETWORK COMMUNICATION; U.S. Ser. No. 11/498,703, filed Aug. 3, 2006, entitled THEFT PREVENTION DEVICE FOR AUTOMOTIVE VEHICLE SERVICE CENTERS; U.S. Ser. No. 11/507,157, filed Aug. 21, 2006, entitled APPARATUS AND METHOD FOR SIMULATING A BATTERY TESTER WITH A FIXED RESISTANCE LOAD; U.S. Ser. No. 11/511,872, filed Aug. 29, 2006, entitled AUTOMOTIVE VEHICLE ELECTRICAL SYSTEM DIAGNOSTIC DEVICE; U.S. Ser. No. 11/519,481, filed Sep. 12, 2006, entitled BROAD-BAND LOW-CONDUCTANCE CABLES FOR MAKING KELVIN CONNECTIONS TO ELECTROCHEMICAL CELLS AND BATTERIES; U.S. Ser. No. 60/847,064, filed Sep. 25, 2006, entitled STATIONARY BATTERY MONITORING ALGORITHMS; U.S. Ser. No. 11/638,771, filed Dec. 14, 2006, entitled BATTERY MONITORING SYSTEM; U.S. Ser. No. 11/641,594, filed Dec. 19, 2006, entitled METHOD AND APPARATUS FOR MEASURING A PARAMETER OF A VEHICLE ELECTRONIC SYSTEM; U.S. Ser. No. 11/711,356, filed Feb. 27, 2007, entitled BATTERY TESTER WITH PROMOTION FEATURE; U.S. Ser. No. 11/811,528, filed Jun. 11, 2007, entitled ALTERNATOR TESTER; U.S. Ser. No. 60/950,182, filed Jul. 17, 2007, entitled BATTERY TESTER FOR HYBRID VEHICLE; U.S. Ser. No. 60/973,879, filed Sep. 20, 2007, entitled ELECTRONIC BATTERY TESTER FOR TESTING STATIONARY BATTERIES; U.S. Ser. No. 11/931,907, filed Oct. 31, 2007, entitled BATTERY MAINTENANCE WITH PROBE LIGHT; U.S. Ser. No. 60/992,798, filed Dec. 6, 2007, entitled STORAGE BATTERY AND BATTERY TESTER; U.S. Ser. No. 12/099,826, filed Apr. 9, 2008, entitled BATTERY RUN DOWN INDICATOR; U.S. Ser. No. 61/061,848, filed Jun. 16, 2008, entitled KELVIN CLAMP FOR ELECTRONICALLY COUPLING TO A BATTERY CONTACT; U.S. Ser. No. 12/168,264, filed Jul. 7, 2008, entitled BATTERY TESTERS WITH SECONDARY FUNCTIONALITY; U.S. Ser. No. 12/174,894, filed Jul. 17, 2008, entitled BATTERY TESTER FOR ELECTRIC VEHICLE; which are incorporated herein in their entirety.

In general, battery testing techniques have used a single, integrated stand-alone unit.

SUMMARY OF THE INVENTION

A cable for connecting to an electronic battery tester is configured to couple to a databus of a vehicle to the electronic battery tester. Electrical connection extending between ends of the cables configured to couple the electronic battery tester to the databus of the vehicle.

DETAILED DESCRIPTION OF THE PREFERRED EMBODIMENTS

Typically, battery testers have been stand-alone units. The present invention provides a battery tester 10 such as that illustrated in FIG. 1 which includes a databus 12 for coupling to external circuitry 14. Battery tester 10 is configured to couple to storage battery 16 through electrical connectors 18 to perform a battery test on battery 16. Connectors 18 can be, for example, Kelvin type connectors. Typically, test circuitry 10 will obtain a dynamic parameter of the battery using an AC forcing function. Examples include dynamic conductance, resistance, admittance, impedance, their combinations, or others. However, any type of battery test can be performed including battery testing which involves application of large loads, or application of large currents or voltages such as through a charger, simple voltage measurements, etc. In one embodiment, the battery tester 10 is permanently mounted in a automotive vehicle such as the type of vehicle that uses a internal combustion engine or an electric engine.

Figure 1:
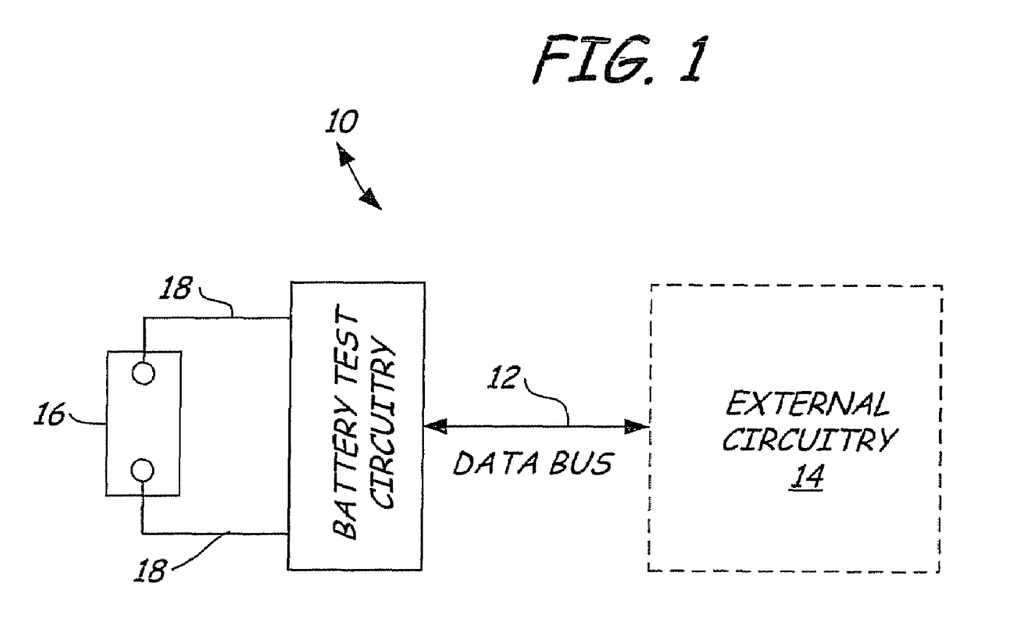
FIG. 1 is a simplified block diagram showing battery test circuitry coupled to external circuitry through a databus.

Databus 12 is used to exchange information with external circuitry 14. Such information includes, for example, raw data measurements and conclusions of battery tester 10, and inputs, such as user inputs and other sensor inputs into battery tester 10. Further, external circuitry 14 can control battery tester 10 through databus 12 and provide information such as a battery rating to battery tester 10 for use in performing a battery test. Databus 12 can be a proprietary databus or can be in accordance with known standards such as RS232, CAN, ISA, PC, PCMCIA, etc. Battery tester 10 can be configured to communicate with portable devices such as portable notebook computers, PDAs (Personal Data Assistants) such as a Palm Pilot™, etc. The databus 12 can also be configured to interface with other types of equipment which are used in the automotive industry such as "scan" tools which are used to interface with the on-board computer in a vehicle. Such scan tools are known in the art and are used to perform diagnostics and retrieve information from the on-board computer. In such an embodiment, databus 12 can be in accordance with the databus used in OBD (on-board diagnostic) systems.

Figure 2:
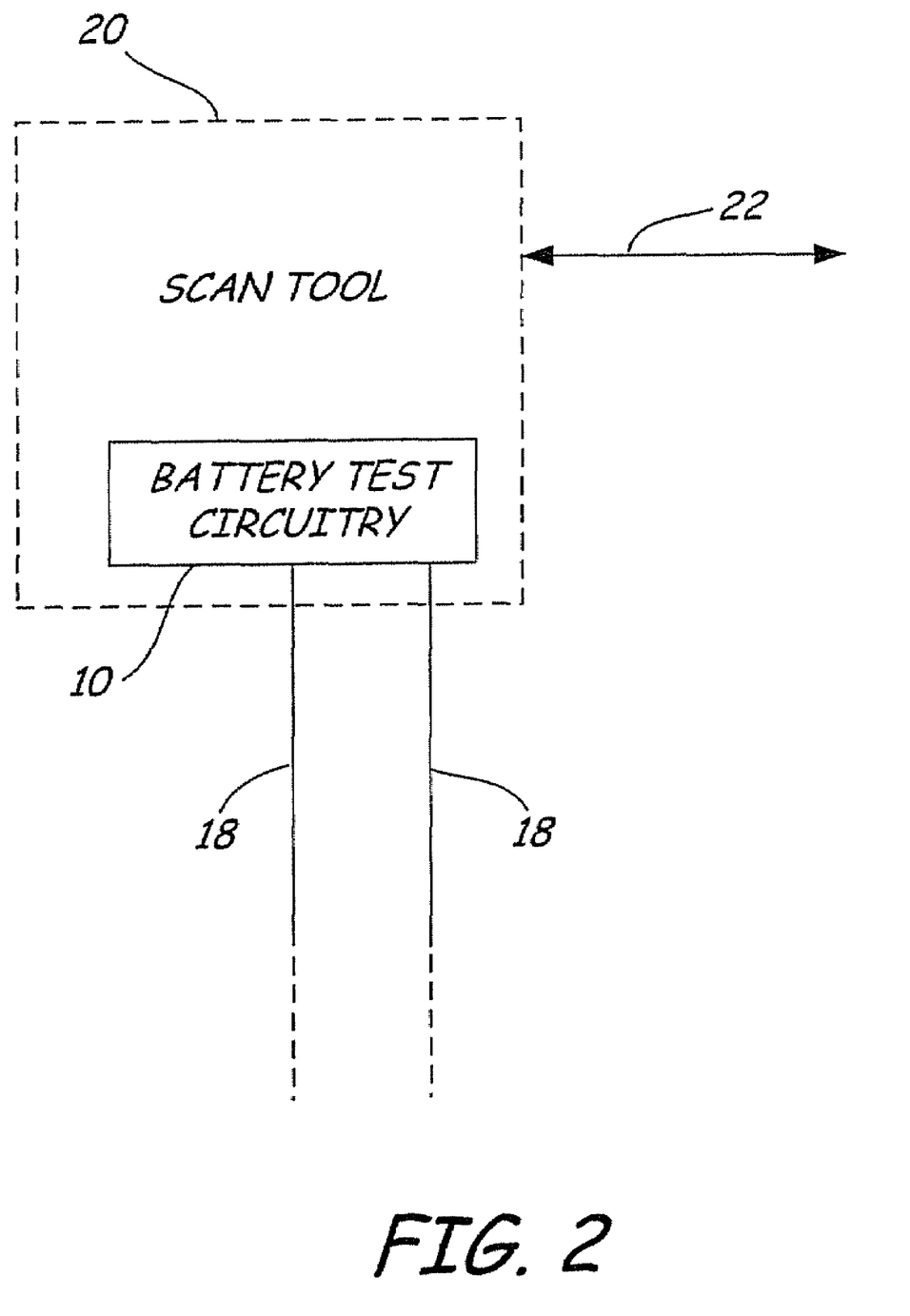
FIG. 2 is a simplified block diagram showing a scan tool which is one type of external circuitry shown in FIG. 1.

The battery tester 10 of FIG. 1 can be a modular component of a scan tool formed by external circuitry 14. In another aspect of the invention as illustrated in FIG. 2, the battery tester 10 is an integral component of a scan tool 20. FIG. 2 also illustrates a second databus 22 which is used to couple to an on-board computer of a vehicle.

In embodiments which utilize a scan tool, an operator is able to perform a battery test using the same scan tool used for diagnosing other conditions of the vehicle. Further, the scan tool can selectively instruct an operator to perform a battery test or control operation of the battery test based upon data retrieved from the on-board vehicle computer system through bus 22. This can be part of an overall diagnostic system used to provide more accurate diagnostics of the vehicle. In one embodiment, the battery test circuitry requires information through bus 22 or monitors the flow of information on a databus of the vehicle. The test circuit can obtain information about battery type, battery rating, and charge history. Additionally, if the vehicle contains an internal battery tester, information regarding battery tests or battery measurements can be obtained or monitored through bus 22. In such an embodiment, test circuit 10 does not need to perform a battery test itself, or couple to the battery.

Figure 3:
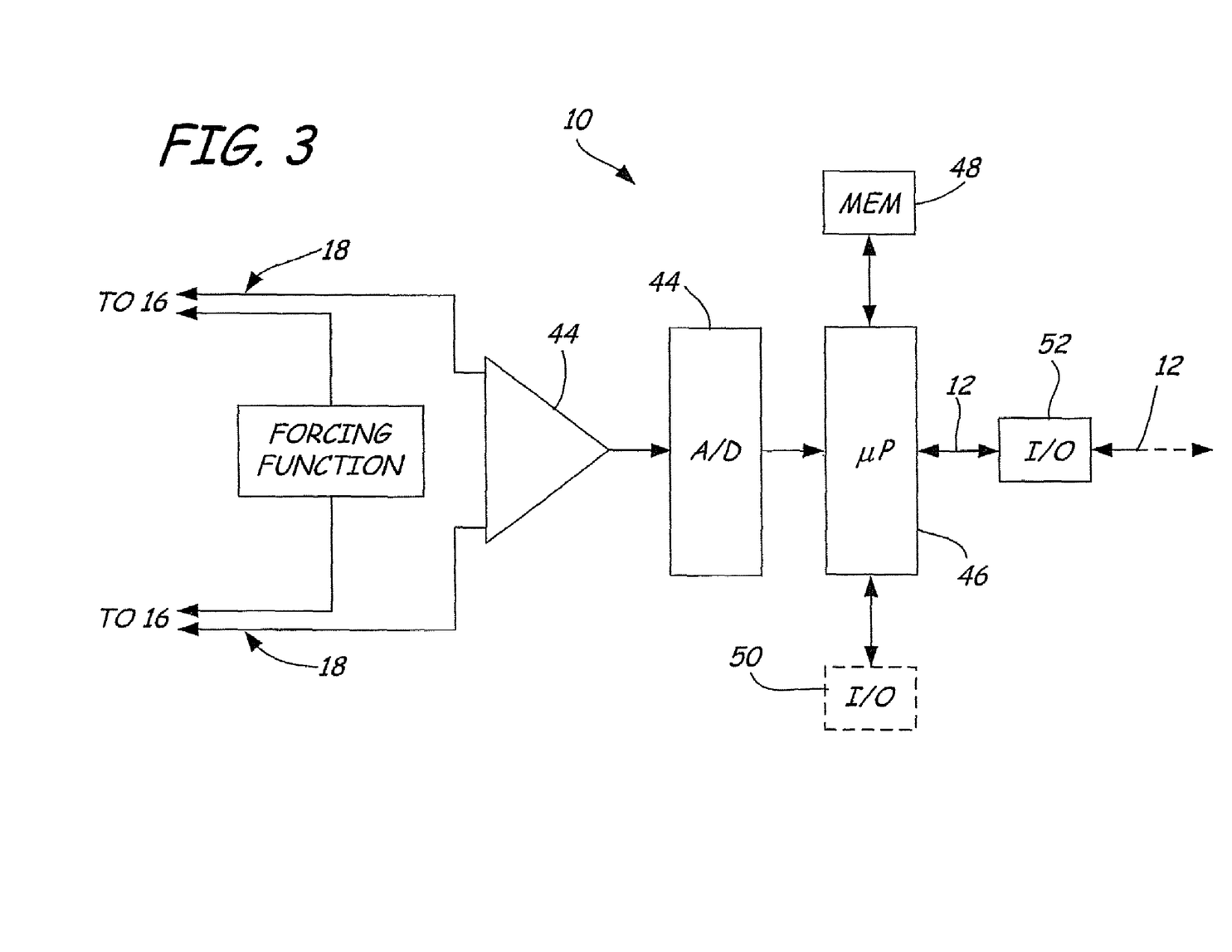
FIG. 3 is a simplified block diagram showing battery test circuitry.

FIG. 3 is a more detailed block diagram of battery test circuitry 10 which includes a forcing function 40 and an amplifier 42 coupled to connectors 18. In the illustration of FIG. 3, connectors 18 are shown as Kelvin connections. The forcing function 40 can be any type of signal which has a time varying component including a transient signal. The forcing function can be through application of a load or by applying an active signal to battery 16. A response signal is sensed by amplifier 42 and provided to analog to digital converter 44 which couples to microprocessor 46. Microprocessor 46 operates in accordance with instructions stored in memory 48. In accordance with the invention, microprocessor 46 can store data into memory 48.

Input/output (I/O) is provided for coupling to the databus 12. I/O 102 can be in accordance with the desired standard or protocol as described above. Data collected by battery test circuitry 10 can be stored in memory 48 and transmitted over bus 12 when pulled by external circuitry 14. In one embodiment, input/output 52 comprises an RF (Radio Frequency) or IR (Infrared) input/output circuit and bus 12 comprises electromagnetic radiation. The logged data can comprise individual measurement points such as voltage and/or current measurements, either static or dynamic. Additionally, the logged data can comprise time and data information, operating conditions such as temperature, charge, etc. In addition to logging raw data, calculated data such as calculated conductance or battery condition, battery state of health, battery state of charge, etc. can be logged.

Of course, the illustration of FIG. 3 is simply one simplified embodiment and other embodiments are in accordance with the invention. Databus 12 may be capable of coupling directly to memory 48 for retrieval of stored data. Additionally, in the illustrated embodiment microprocessor 46 is configured to measure a dynamic parameter based upon the forcing function 40. This dynamic parameter can be correlated with battery condition as set forth in the above-mentioned Champlin and Midtronics, Inc. patents. However, other types of battery tests circuitry can be used in the present invention and certain aspects of the invention should not be limited to the specific embodiment illustrated herein. FIG. 3 also illustrates an optional input/output block 50 which can be any other type of input and/or output coupled to microprocessor 46. For example, this can be used to couple to external devices or to facilitate user input and/or output. Databus 12 can also be used to provide data or instructions to microprocessor 46. This can instruct the microprocessor 46 to perform a certain test, transmit specified data, update programming instructions, constant test parameters, etc. stored in memory 48. Although a microprocessor 46 is shown, other types of computational or other circuitry can be used to collect and place data into memory 48.

In one embodiment, I/O 50 comprises an interface to a removable digital storage medium, for example a Secure Digital (SD) card. Similarly, the I/O 50 can be configured to provide a multimedia interface to an MMC card. The databus 12 can be in accordance with any particular standard or otherwise for use in communicating with a scan tool. Additional examples includes RS-485, current loops, J1939, J1850 or a CAN bus.

Figure 4:
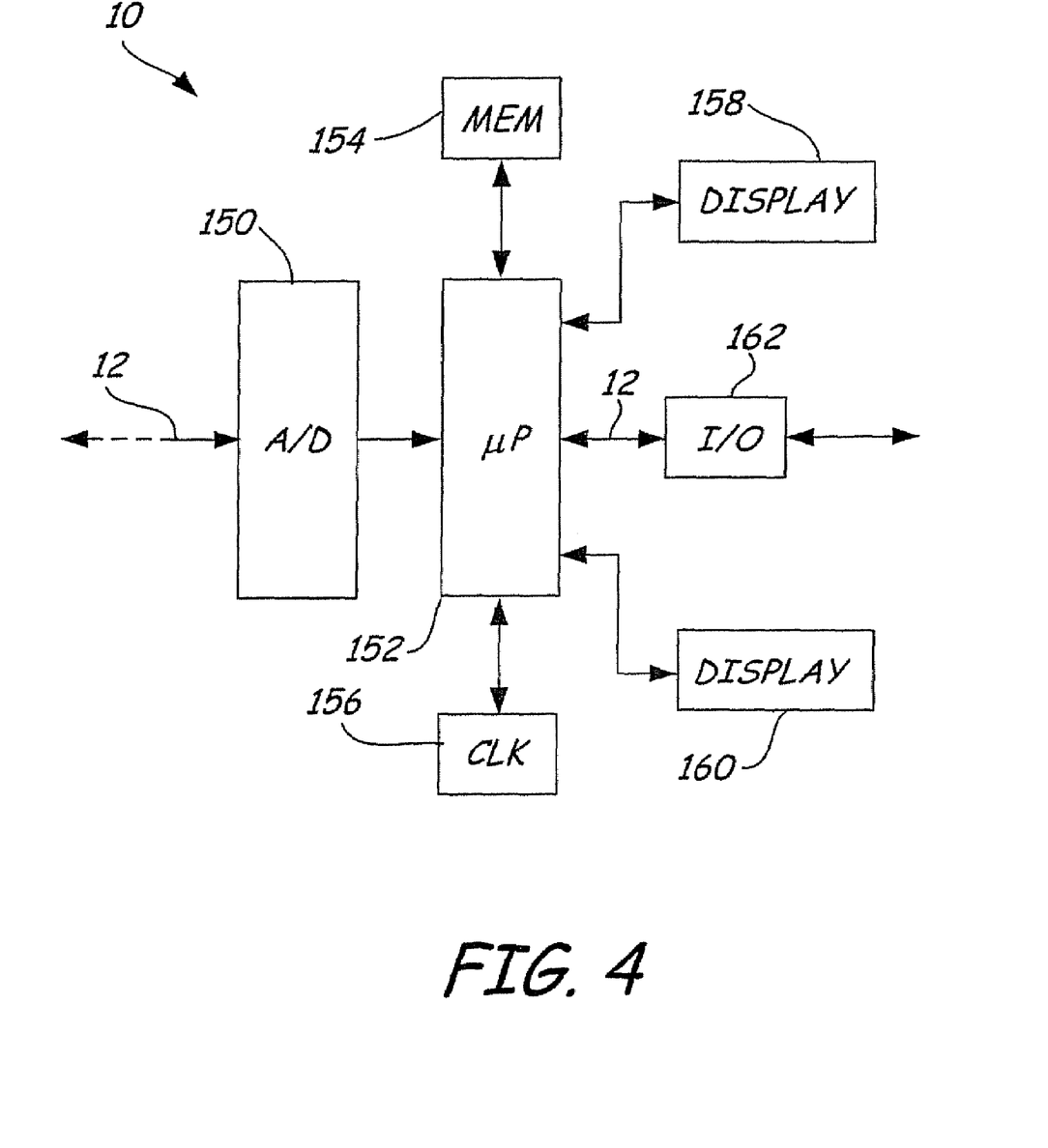
FIG. 4 is a simplified block diagram of external circuitry configured to couple to the battery test circuitry of FIG. 3.

FIG. 4 is a more detailed block diagram of external circuitry 14. External circuitry 14 includes input/output (I/O) circuitry 150 for coupling to databus 12. Again, if databus 12 is through a non-physical connections such as infrared or radio frequency, I/O circuitry 150 should operate accordingly. A microprocessor 152 couples to memory 154 and operates at a rate determined by a system clock 156. Microprocessor 152 can provide an output through display 158 and receive input from an operator through input 160. In operation, circuitry 14 is operably coupled to battery test circuitry through databus 12 and is configured to send and receive information through databus 12. An operator can instruct microprocessor 152 or microprocessor 152 can operate automatically, to retrieve data from memory 48 in battery test circuitry 10. The microprocessor 152 can process the data to calculate battery condition and follow trends in the measured values retrieved from memory 48. This information can be used to diagnose the condition of the battery 16 as well as use a charge and discharge history experienced by battery 16. Further, the information can be used to validate warranty claims in which a battery is returned to a manufacturer under a claim that it is defective.

External circuitry 14 can include additional input, output or input/output circuits 162 for communication using other techniques. For example, data can be sent to a printer or other computer system. Any type of data link can be used including modems, Ethernet or networking connections, etc.

In one embodiment, the external circuitry 14 comprises a personal data assistant (PDA) such as a Palm Pilot™. In such an embodiment, I/O 100 in battery test circuitry 10 can comprise a cradle which is adapted to receive the PDA. In such an embodiment, the PDA can simply be "dropped" into the cradle in order to exchange data with test circuitry 10. Similarly, many PDAs include an infrared or RF link which can be used to exchange data with battery test circuitry 10.

As discussed above, the battery tester circuitry 10 can be a modular component of a scan tool. For example, that scan tool can comprise external circuitry 14 shown in FIG. 1 and the databus 12 can be part of a cabling connection between the battery test circuitry 10 and the scan tool 14. In such an embodiment, there are a number of implementations of the present invention. In one aspect, all of the test circuitry necessary for performing a battery test if contained in the battery test circuitry 10. The final result of the battery test is provided to the scan tool 14 over the databus. Further, operator instructions or display data can be provided to the scan tool 14 and the battery test circuitry 10 can utilize a display 158, I/O 162, input 160 or other circuitry available in the scan tool 14. In another example, the microprocessor 152 of the scan tool 14 performs any calculations used in a battery test, and the battery test circuitry 10 includes less complex components such as the analog components required for performing a battery test. For example, the test circuitry 10 can contain the forcing function 40 and sensor 42. Analog values can be provided to the scan tool 14 and then digitize the received analog values. In another example, the analog values are digitized within the battery test circuitry 10 and provides it in a digital format to the scan tool 14. In another example embodiment, microprocessor 46 of the battery test circuitry 10 and microprocessor 152 of scan tool 14 are both utilized in a battery test. For example, the microprocessor 152 of the scan tool 14 can compute conversions between various rating systems, particular test requirements for certain types of vehicles or batteries or other higher level functions. The microprocessor 46 of the battery test circuitry 10 determines the initial battery test results.

In other example embodiments, the battery test circuitry 10 continually broadcasts voltage and/or conductance, current and/or conductance measurements of the databus 12. The battery test circuitry 10 can have an internal power source, be powered from the battery under test 16, or receive power from the scan tool 14. The databus 12 can be used to carry text messages to scan tool 14 for display on display 158 or in another manner. In another example, the memory 154 of the scan tool 14 contains a set of messages. A token or other short hand representation of a text message is transmitted from the battery test circuitry to the scan tool 14 on databus 12. This causes the microprocessor 152 to retrieve a selected message from the memory 154 which can then be displayed on display 158 or otherwise provided as an output. In one embodiment, the battery test circuitry provides an indication of the relative condition of the battery, for example, "good", "good/recharge", "charge and retest", or "replace battery". Another example condition is "bad cell-replace". If text messages are contained in a memory of the battery tester 10, the text can be in an appropriate language for the consumer.

In various aspects, the battery test circuitry 10 does not use Kelvin connections. In another example embodiment, a small or large load is included in the battery test circuitry 10. The load is used to apply a load test to the battery. In such an embodiment, the battery test circuitry may operate exclusively based upon such a load test and does not include circuitry to measure a dynamic parameter of the battery 12. In another example, the battery test is based upon a load test as well as a dynamic parameter based test. In another example, the battery test circuitry 10 includes a display for locally displaying information. One type of display includes a simple optical output such as that provided by one or more LEDs. The color or number of LEDs can indicate the result of a battery test. In some embodiments information beyond a battery test can be displayed by the scan tool 14. For example, the scan tool can display voltage, conductance, battery condition, battery cold cranking amps (CCA), a minimum or a maximum sensed voltage, or other measurements. The battery test circuitry 10 can be integrated with a cable that plugs into the scan tool 14. For example, the battery test circuitry 10 can be included in a small housing having one cable for connection to the scan tool 14 and another cable or cables for connections to the battery 12.

In some embodiments, battery test circuitry 10 can include circuitry configured to charge battery 16. In such embodiments, memory 48 can be used to log information regarding any charge which is applied to battery 16.

Figure 5:
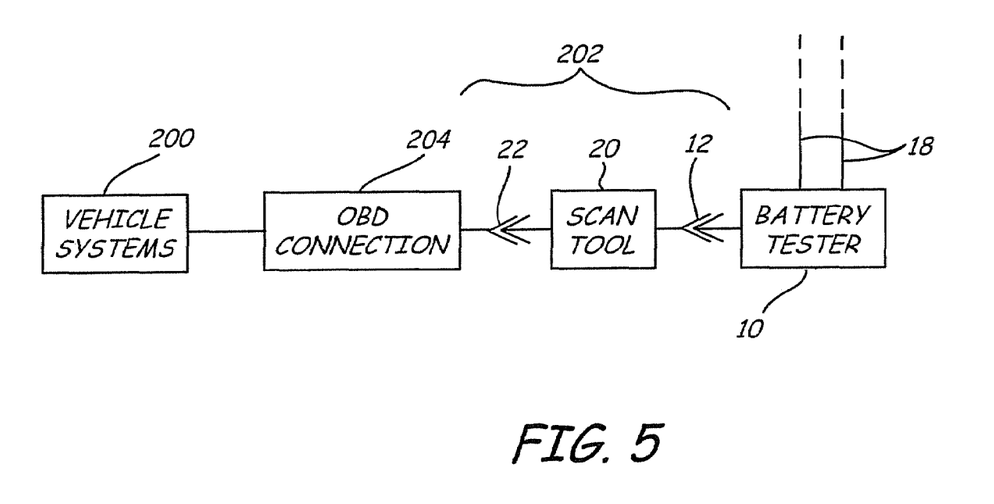
FIG. 5 is a simplified block diagram showing connection of a battery tester to an on board database of a vehicle via a scan tool.
Figure 6:
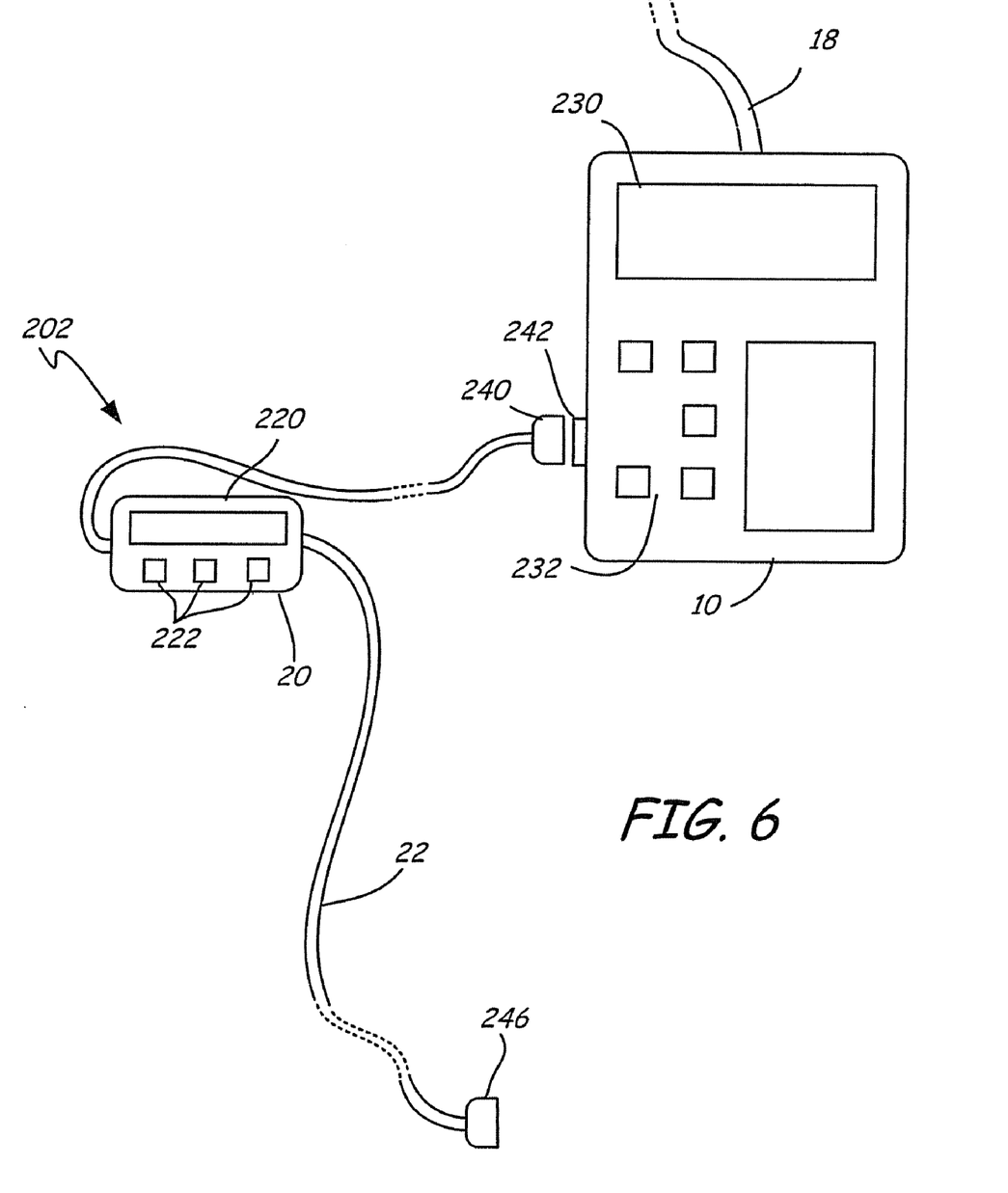
FIG. 6 is a perspective view of a cable including a scan tool used to couple a battery tester to a vehicle.

FIG. 5 is another example embodiment of the present invention in which a scan tool 20 is used to couple the battery test circuitry 10 to vehicle systems 200. The scan tool 20 can be embodied, for example, in a cable 202. The scan tool 20 couples to vehicle electrical systems 200 through, for example, the on board diagnostic connection 204 to the vehicle. Battery tester circuitry 10 couples to the scan tool 20 through a databus 12. It can be, for example, plugged in to the scan tool 20. Kelvin connections 18 are also provided for coupling to a battery in performing a battery test. FIG. 6 is a view of the battery tester circuitry 10 configured to couple to cable 202 which contains scan tool 20. Scan tool 20 is shown with an optional display 220 and user inputs 222 such as buttons. The battery tester 10 is illustrated as having a display 230 and user input buttons 232. Other types input output configurations can also be provided. Cable 202 includes a plug 240 configured to plug into plug 242 on battery tester 10.

Further, cable 202 includes an OBD plug 246 configured to plug into an OBD connection on a vehicle. During operation, the scan tool 20 can be operated using the display 220 and the input buttons 222, if provided, or by circuitry within battery tester circuitry 10. In some embodiments, the cable 202 simply provides an interface between the tester 10 and the vehicle database and any scan tool functionality is performed within the battery tester circuitry 10. In another embodiment, active electronics are provided within the cable 202 to provide data conversion, scan tool functions and/or other functionality as desired.

Figure 7:
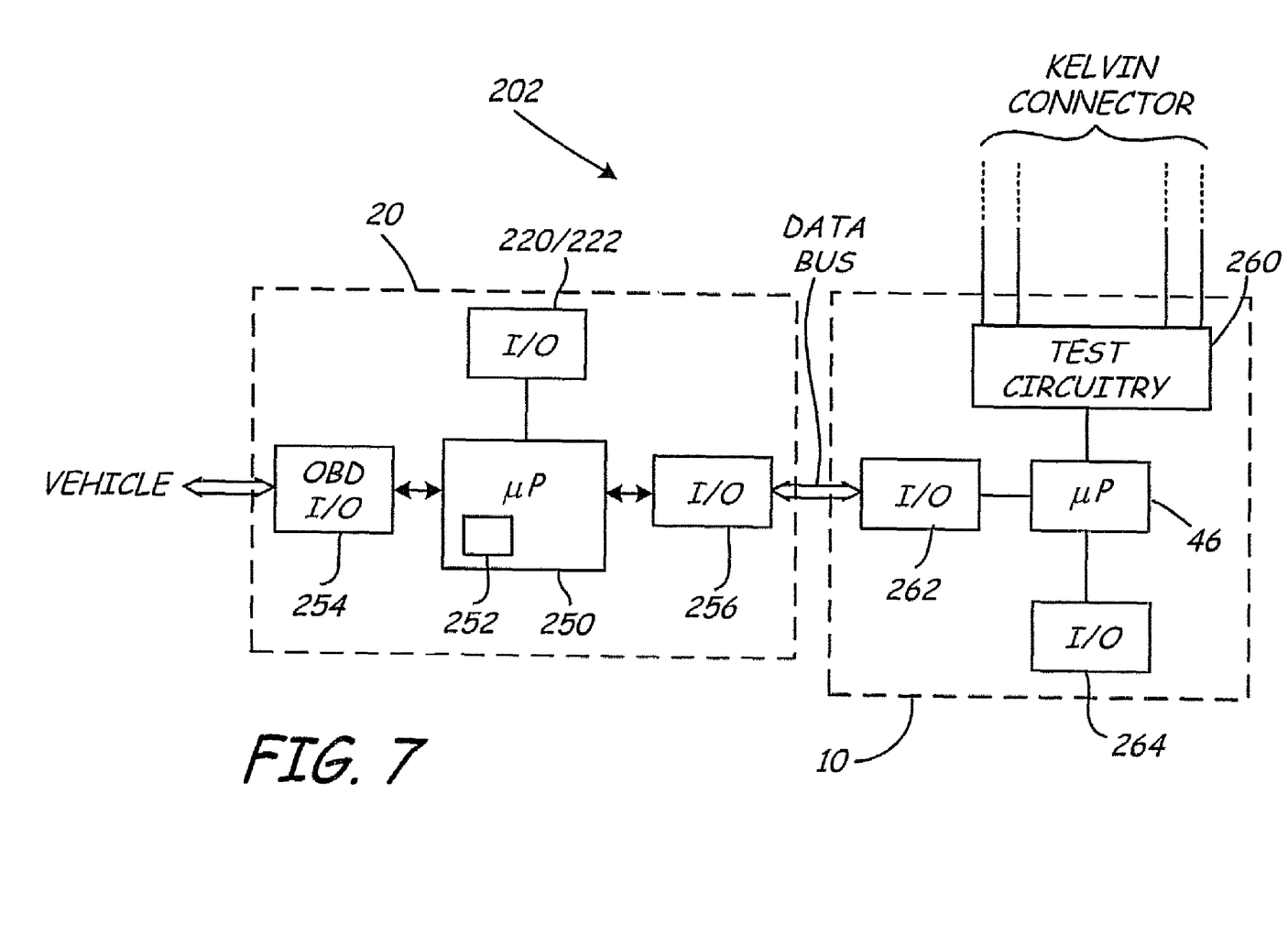
FIG. 7 is a simplified block diagram of the scan tool and battery tester shown in FIG. 6.

FIG. 7 is a blocked diagram showing various components illustrated in FIG. 6. In FIG. 7, the scan tool 20 includes a microprocessor 250 having a memory 252. OBD input/output circuitry 254 is provided for coupling to the on board database of the vehicle. IO circuitry 256 is used for communication with battery tester 10. Data in memory 252 can be updated by the battery tester, for example through the use of a smart card or other digital storage device. Battery tester 10 includes I/O circuitry 262 for coupling to the scan tool 20. The microprocessor 46 couples to test circuitry 260 and input/output circuitry 264. Test circuitry 260 is illustrated as a block diagram representation of the test circuitry used to perform a battery test through a Kelvin connection. The test circuitry can be analog and/or digital circuitry and may be, for example, partially implemented in microprocessor 46. The scan tool circuitry can receive power from an internal or external source including receiving power from the electronic battery tester.

Although the various connections between components shown here are illustrated as being wire connections, the invention is also applicable with wireless connections such as using rf, ir, inductive coupling or through other techniques. By providing the battery test circuitry with access to the on board database of the vehicle, additional information can be garnered regarding operation of the vehicle and, in some configurations, operation of the vehicle can be controlled or otherwise configured. In another example configuration, the IO circuitry to communicate with a smart card or other storage medium for use in updating software within the scan tool and/or battery tester.

Although the present invention has been described with reference to preferred embodiments, workers skilled in the art will recognize that changes may be made in form and detail without departing from the spirit and scope of the invention. For example, any type of battery test or battery test circuitry can be used by battery tester 10. Further, the databus 12 can be in accordance with any databus technique and should not be limited to the examples set forth herein. In various embodiments, battery tester 10 can be powered through power received through battery 16 or can be powered through power received through databus 12 or from a scan tool.

What is claimed is:

1. An electronic battery tester for testing a storage battery of an automotive vehicle, comprising:
   Kelvin connectors configured to electrically couple to the storage battery;
   forcing functional circuitry configured to apply a forcing function to the battery though the Kelvin connectors;
   measurement circuitry configured to determine a condition of the storage battery based upon a dynamic parameter of the storage battery measured through the Kelvin connectors in response to the forcing function;
   a databus configured to receive data; and
   wherein the determined condition of the storage battery is further a function of the received data.

2. The apparatus of the claim 1 wherein the databus comprises a non-physical connection.

3. The apparatus of claim 2 wherein the non-physical connection comprises a radio frequency (RF) connection.

4. The apparatus of claim 2 wherein the non-physical connection comprises a infrared (IR) connection.

5. The apparatus of claim 1 wherein the received data comprises battery rating.

6. The apparatus of claim 1 wherein the received data comprises battery type.

7. The apparatus of claim 1 wherein the received data comprises a charged history of the storage battery.

8. The apparatus of claim 1 wherein the received data comprises information regarding storage battery tests.

9. The apparatus of claim 1 wherein the received data comprises information regarding storage battery measurement.

10. The apparatus of claim 1 wherein the databus is configured to couple to the Kelvin connectors and receive data based upon a response of the storage battery to the applied forcing function as measured using the Kelvin connectors.

11. The apparatus of claim 1 wherein the databus is configured to communicate with a personal data assistant (PDA).

12. The apparatus of claim 11 wherein the databus includes a cradle configured to couple to the personal data assistant.

13. The apparatus of claim 1 wherein the databus is configured to control operation of the vehicle.

14. The apparatus of claim 1 wherein the databus is configured to couple to the vehicle and retrieve information regarding operation of the vehicle.

* * * * *